(12) United States Patent
Jonasson et al.

(10) Patent No.: US 10,028,845 B2
(45) Date of Patent: Jul. 24, 2018

(54) PUMP MECHANISM

(71) Applicant: Ossur Iceland ehf, Reykjavik (IS)

(72) Inventors: Hafsteinn Jonasson, Mosfellsbær (IS); Hallgrimur Skuli Hafsteinsson, Hafnarfjordur (IS); Egill Sveinbjorn Egilsson, Reykjavik (IS); Dana Stewart Marlin, Hafnarfjordur (IS); Marco Steinberg, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 14/988,503

(22) Filed: Jan. 5, 2016

(65) Prior Publication Data

US 2016/0199202 A1 Jul. 14, 2016

Related U.S. Application Data

(60) Provisional application No. 62/151,518, filed on Apr. 23, 2015, provisional application No. 62/101,154, filed on Jan. 8, 2015.

(51) Int. Cl.
*A61F 2/68* (2006.01)
*A61F 2/66* (2006.01)
(Continued)

(52) U.S. Cl.
CPC .................. *A61F 2/68* (2013.01); *A61F 2/66* (2013.01); *A61F 2/80* (2013.01);
(Continued)

(58) Field of Classification Search
CPC ...... A61F 2/80; A61F 2/68; A61F 2/66; A61F 2002/501; A61F 2002/5067; A61F 2002/5079; A61F 2002/607
(Continued)

(56) References Cited

U.S. PATENT DOCUMENTS 708,685 A 9/1902 White
980,457 A 1/1911 Toles
(Continued)

FOREIGN PATENT DOCUMENTS

AU 670631 B2 7/1996
BE 675 386 A 5/1966
(Continued)

OTHER PUBLICATIONS

Brochure, "Sometimes Less is More, Harmony P3" Otto Bock, 12 pages. Available at, http://www.ottobock.com/cps/rde/xbcr/ob_es/646A303-EN-01-1001w.pdf", dated 2012.
(Continued)

*Primary Examiner* — Alvin Stewart
(74) *Attorney, Agent, or Firm* — Workman Nydegger

(57) ABSTRACT

A prosthetic system includes a prosthetic foot with a foot member defining a first end portion, a second end portion, and an intermediate portion defining a curvature and extending between the first and second end portions. A pump mechanism is coupled to the foot member. The pump mechanism includes a housing defining a cavity, and a membrane situated in the cavity. The pump mechanism is movable between an original configuration and an expanded configuration. A movable member includes a first portion coupled to the membrane and a second portion arranged to slidably engage the foot member. Relative movement between the first and second end portions moves the first portion of the movable member relative to the housing and slides the second portion along a length of the foot member to shift the pump mechanism between the original and expanded configurations.

20 Claims, 14 Drawing Sheets

(51) Int. Cl.
    *A61F 2/80*         (2006.01)
    *A61F 2/74*         (2006.01)

(52) U.S. Cl.
    CPC ............... *A61F 2002/6614* (2013.01); *A61F 2002/6664* (2013.01); *A61F 2002/6671* (2013.01); *A61F 2002/745* (2013.01); *A61F 2002/748* (2013.01); *A61F 2002/805* (2013.01)

(58) Field of Classification Search
    USPC .............................................. 623/36, 53–56
    See application file for complete search history.

(56) References Cited

U.S. PATENT DOCUMENTS

| | | |
|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A * | 8/1996 | Caspers ............... A61F 2/5046 623/24 |
| 5,555,216 A | 9/1996 | Drouot |
| 5,571,208 A | 11/1996 | Caspers |
| 5,593,454 A | 1/1997 | Helmy |
| D379,845 S | 6/1997 | Lee |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A * | 4/1998 | Caspers ............... A61F 2/5046 623/34 |
| 5,807,303 A | 9/1998 | Bays |
| 5,830,237 A | 11/1998 | Kania |
| 5,846,063 A | 12/1998 | Lakic |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,508,842 B1 * | 1/2003 | Caspers ............... A61F 2/5046 623/32 |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosier et al. |
| 6,797,008 B1 | 9/2004 | Arbogast et al. |
| D499,794 S | 12/2004 | Comer |
| 6,855,170 B2 | 2/2005 | Gramnas |
| 6,863,695 B2 | 3/2005 | Doddroe et al. |
| 6,926,742 B2 | 8/2005 | Caspers et al. |

(56) References Cited

U.S. PATENT DOCUMENTS

| | | |
|---|---|---|
| 6,964,688 B1 | 11/2005 | Kania |
| 6,969,408 B2 | 11/2005 | Lecomte et al. |
| 6,974,484 B2 | 12/2005 | Caspers |
| 7,025,792 B2* | 4/2006 | Collier .................. A61F 2/60 623/33 |
| 7,025,793 B2 | 4/2006 | Egilsson |
| D526,046 S | 8/2006 | Lin |
| 7,255,131 B2 | 8/2007 | Paper et al. |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2* | 12/2008 | Collier .................. A61F 2/60 623/33 |
| 7,686,848 B2 | 3/2010 | Christensen |
| 7,744,653 B2 | 6/2010 | Rush et al. |
| D634,813 S | 3/2011 | Hernandez, IV |
| 7,909,884 B2 | 3/2011 | Egilsson et al. |
| 7,922,775 B2 | 4/2011 | Caspers |
| 7,947,085 B2* | 5/2011 | Haines .................. A61F 2/68 623/24 |
| D639,825 S | 6/2011 | Murakami et al. |
| 7,993,413 B2 | 8/2011 | Perkins et al. |
| 8,007,543 B2 | 8/2011 | Martin |
| 8,034,120 B2 | 10/2011 | Egilsson et al. |
| 8,052,760 B2 | 11/2011 | Egilsson et al. |
| 8,080,065 B2 | 12/2011 | Scussel et al. |
| 8,097,043 B2 | 1/2012 | Egilsson |
| 8,097,766 B2 | 1/2012 | Carlson et al. |
| 8,114,167 B2 | 2/2012 | Caspers |
| D655,393 S | 3/2012 | Whitaker |
| D656,223 S | 3/2012 | Cronje et al. |
| 8,298,294 B2 | 10/2012 | Kaltenborn et al. |
| 8,317,876 B2 | 11/2012 | Mosler |
| 8,343,233 B2 | 1/2013 | Perkins et al. |
| D675,714 S | 2/2013 | Nguyen |
| D681,782 S | 5/2013 | Bohm et al. |
| 8,523,951 B2 | 9/2013 | Kania |
| D691,240 S | 10/2013 | Iranyi et al. |
| D691,701 S | 10/2013 | Iranyi et al. |
| D691,702 S | 10/2013 | Iranyi et al. |
| D691,703 S | 10/2013 | Iranyi et al. |
| D702,320 S | 4/2014 | Pifer |
| 8,956,422 B2 | 2/2015 | Halldorsson |
| 8,961,618 B2 | 2/2015 | Lecomte et al. |
| 9,017,421 B2 | 4/2015 | Lecomte et al. |
| 9,044,348 B2* | 6/2015 | Halldorsson ............ A61F 2/80 |
| 9,066,821 B2 | 6/2015 | Egilsson et al. |
| 9,066,822 B2 | 6/2015 | Caldwell et al. |
| 9,072,617 B2* | 7/2015 | Halldorsson ............ A61F 2/80 |
| 9,198,790 B2 | 12/2015 | Babkes et al. |
| 9,259,332 B2* | 2/2016 | Danzig .................. A61F 2/68 |
| 9,486,335 B2* | 11/2016 | Halldorsson ............ A61F 2/80 |
| 2001/0005798 A1 | 6/2001 | Caspers |
| 2001/0016781 A1 | 8/2001 | Caspers |
| 2002/0087215 A1 | 7/2002 | Caspers |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0030411 A1 | 2/2004 | Caspers |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131324 A1 | 6/2005 | Bledsoe |
| 2005/0131549 A1 | 6/2005 | Caspers |
| 2005/0143838 A1* | 6/2005 | Collier .................. A61F 2/60 623/34 |
| 2005/0240282 A1 | 10/2005 | Rush et al. |
| 2005/0267603 A1 | 12/2005 | Lecomte et al. |
| 2006/0212130 A1* | 9/2006 | Collier .................. A61F 2/60 623/26 |
| 2006/0212131 A1 | 9/2006 | Curtis |
| 2007/0005149 A1 | 1/2007 | Egilsson et al. |
| 2007/0043316 A1 | 2/2007 | Carlson et al. |
| 2007/0055383 A1 | 3/2007 | King |
| 2007/0112440 A1 | 5/2007 | Perkins et al. |
| 2007/0196222 A1 | 8/2007 | Mosler et al. |
| 2007/0204487 A1 | 9/2007 | Clough |
| 2007/0213839 A1* | 9/2007 | Nachbar ................. A61F 2/60 623/26 |
| 2008/0086218 A1 | 4/2008 | Egilsson |
| 2008/0147202 A1* | 6/2008 | Danzig .................. A61F 2/68 623/26 |
| 2008/0147204 A1* | 6/2008 | Ezenwa ................. A61F 2/68 623/33 |
| 2008/0243266 A1* | 10/2008 | Haynes .................. A61F 2/68 623/34 |
| 2008/0269911 A1* | 10/2008 | Street .................. A61F 2/68 623/26 |
| 2008/0269912 A1 | 10/2008 | Gobbers et al. |
| 2009/0036998 A1* | 2/2009 | Finlinson ............ A61F 2/78 623/34 |
| 2009/0132056 A1 | 5/2009 | Kania |
| 2009/0157196 A1* | 6/2009 | Danzig .................. A61F 2/68 623/34 |
| 2009/0198346 A1 | 8/2009 | Perkins et al. |
| 2009/0204229 A1 | 8/2009 | Mosler et al. |
| 2009/0281637 A1* | 11/2009 | Martin .................. A61F 2/68 623/34 |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1* | 12/2010 | Caspers ................ A61F 2/66 623/34 |
| 2010/0331749 A1 | 12/2010 | Powaser |
| 2011/0035027 A1 | 2/2011 | McCarthy |
| 2011/0046748 A1* | 2/2011 | Martin .................. A61F 2/68 623/34 |
| 2011/0060421 A1 | 3/2011 | Martin et al. |
| 2011/0071649 A1 | 3/2011 | McKinney |
| 2011/0087142 A1 | 4/2011 | Ravikumar et al. |
| 2011/0125291 A1* | 5/2011 | Tompkins ............. A61F 2/68 623/34 |
| 2011/0130846 A1 | 6/2011 | Kampas et al. |
| 2011/0202143 A1* | 8/2011 | Caspers ................ A61F 2/5046 623/36 |
| 2011/0270413 A1 | 11/2011 | Haynes |
| 2011/0295386 A1 | 12/2011 | Perkins et al. |
| 2012/0000092 A1 | 1/2012 | Ingvarsson et al. |
| 2012/0035520 A1 | 2/2012 | Ingimundarson et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1 | 4/2013 | Caldwell et al. |
| 2013/0211544 A1 | 8/2013 | Jonsson et al. |
| 2013/0282142 A1 | 10/2013 | Perkins et al. |
| 2013/0289741 A1* | 10/2013 | Halldorsson ............ A61F 2/80 623/34 |
| 2014/0249648 A1 | 9/2014 | Sandahl |
| 2015/0238331 A1* | 8/2015 | Halldorsson ............ A61F 2/80 623/34 |
| 2015/0282954 A1* | 10/2015 | Halldorsson ............ A61F 2/80 623/34 |
| 2016/0120665 A1 | 5/2016 | Muller |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685861 C | 12/1939 |

(56) References Cited

FOREIGN PATENT DOCUMENTS

| | | |
|---|---|---|
| DE | 745 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | 7155343 A | 6/1995 |
| SE | 8801686 | 3/1989 |
| SU | 1667855 A1 | 8/1991 |
| SU | 1771722 A1 | 10/1992 |
| SU | 1812982 A3 | 4/1993 |
| SU | 1821177 A1 | 6/1993 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |
| WO | 01/54631 A1 | 8/2001 |
| WO | 01/70147 A2 | 9/2001 |
| WO | 02/026158 A2 | 4/2002 |
| WO | 02/065958 A2 | 8/2002 |
| WO | 02/067825 A2 | 9/2002 |
| WO | 02/080813 A2 | 10/2002 |
| WO | 03/077797 A2 | 9/2003 |
| WO | 03/099173 A1 | 12/2003 |
| WO | 03/099188 A1 | 12/2003 |
| WO | 2005/039444 A2 | 5/2005 |
| WO | 2005/105000 A1 | 11/2005 |
| WO | 2006/012820 A1 | 2/2006 |
| WO | 2010/141960 A2 | 12/2010 |
| WO | 2011/035099 A1 | 3/2011 |
| WO | 2012010309 A1 | 1/2012 |
| WO | 2012/177965 A1 | 12/2012 |
| WO | 2014194998 A1 | 12/2014 |

OTHER PUBLICATIONS

Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.

Brochure, "Harmony Certification Course Manual," Original Harmony Pump, 42 pages. Availible at, http://academy.ottobockus.com/videos/harmony/data/downloads/harmony%20course%20manual%202013.pdf. Dated 2013.

Brochure, Harmony P2 & HD, 2 pages. Available at http://www.ottobock.com/cps/rde/xchg/ob_us_en/hs.xsl/14904.html?id=4641. Dated 2012.

International Search Report from corresponding PCT Application No. PCT/US2013/025849, dated Jun. 4, 2013.

International Search Report and Written Opinion Regarding Application No. PCT/US2013/038668, dated Aug. 7, 2013.

Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.

International Search Report and Written Opinion from Corresponding International PCT Application No. PCT/US2014019218, dated May 9, 2014.

International Search Report from corresponding International PCT Application No. PCT/US2015/041089, dated Oct. 5, 2015.

International Search Report from corresponding International PCT Application No. PCT/US2015/044434, dated Oct. 8, 2015.

International Search Report and Written Opinion from corresponding International PCT Application No. PCT/US2014/019218, dated May 9, 2014.

International Search Report from PCT Application No. PCT/US2015/044434, dated Oct. 8, 2015.

International Search Report from PCT Application No. PCT/US2015/041089, dated Oct. 5, 2015.

International Search Report from PCT Application No. PCT/US2016/012215, dated May 23, 2016.

International Search Report from PCT Application No. PCT/US2016/033707, dated Jul. 29, 2016.

International Search Report from corresponding PCT Application No. PCT/US2016/033915, dated Jul. 29, 2016.

Chinese Examination Report from Chinese Application No. 201380022874.0, dated Aug. 25, 2015.

International Search Report from corresponding International PCT Application No. PCT/US2015/037204, dated Sep. 25, 2015.

International Preliminary Report on Patentability From PCT Application No. PCT/US2016/012215, dated Jul. 11, 2017.

* cited by examiner

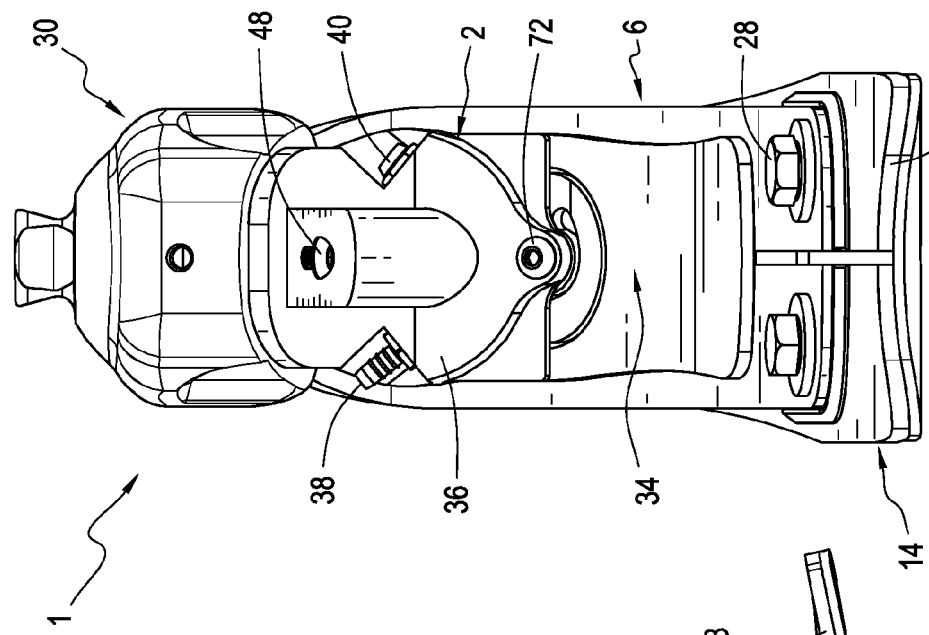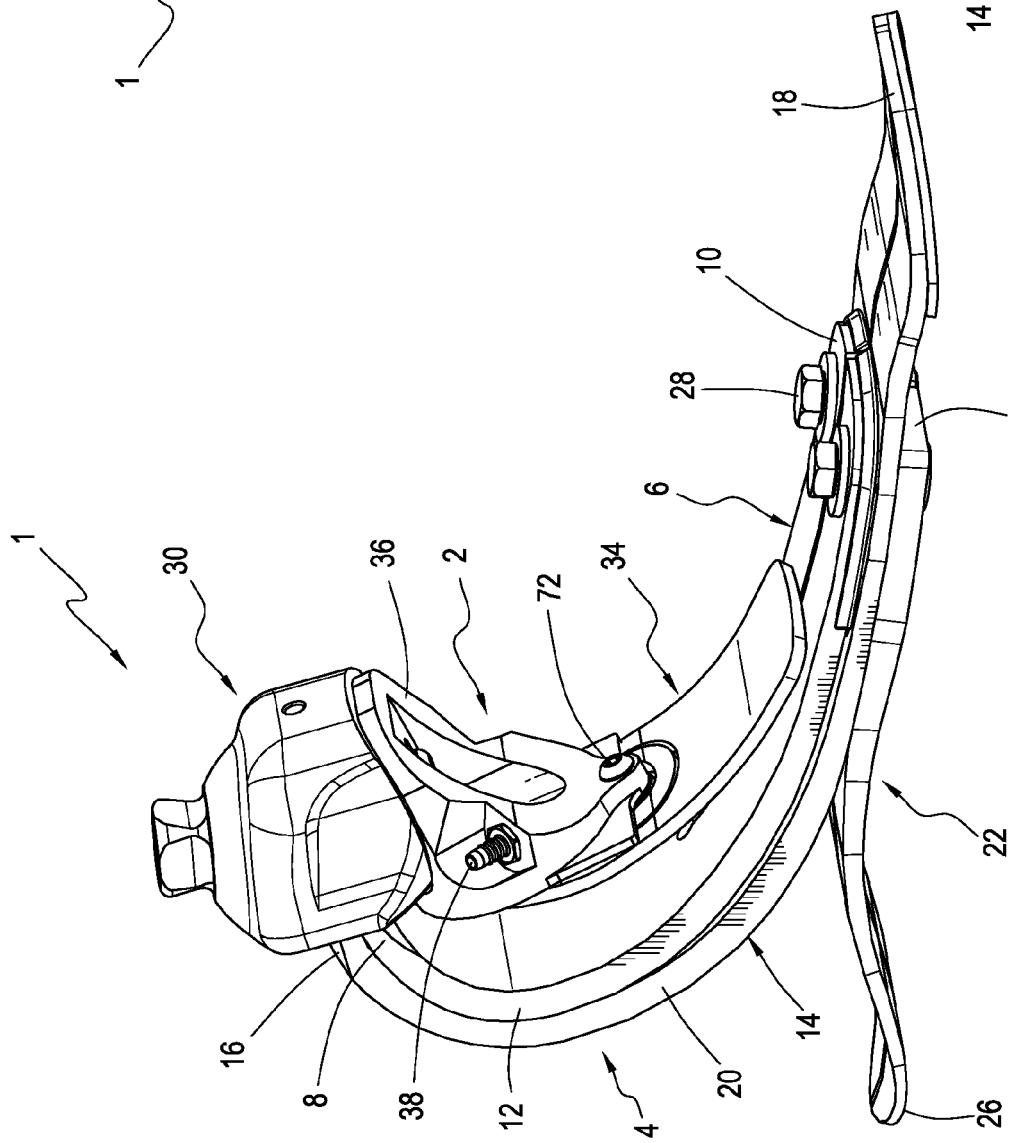

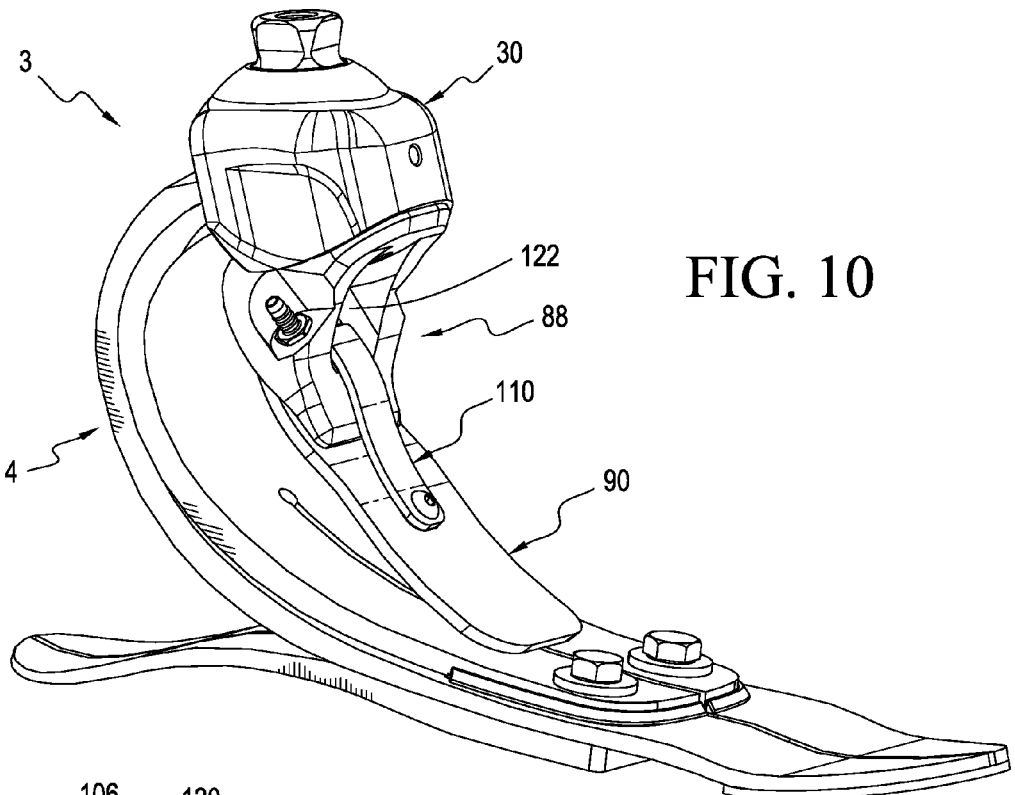
FIG. 10
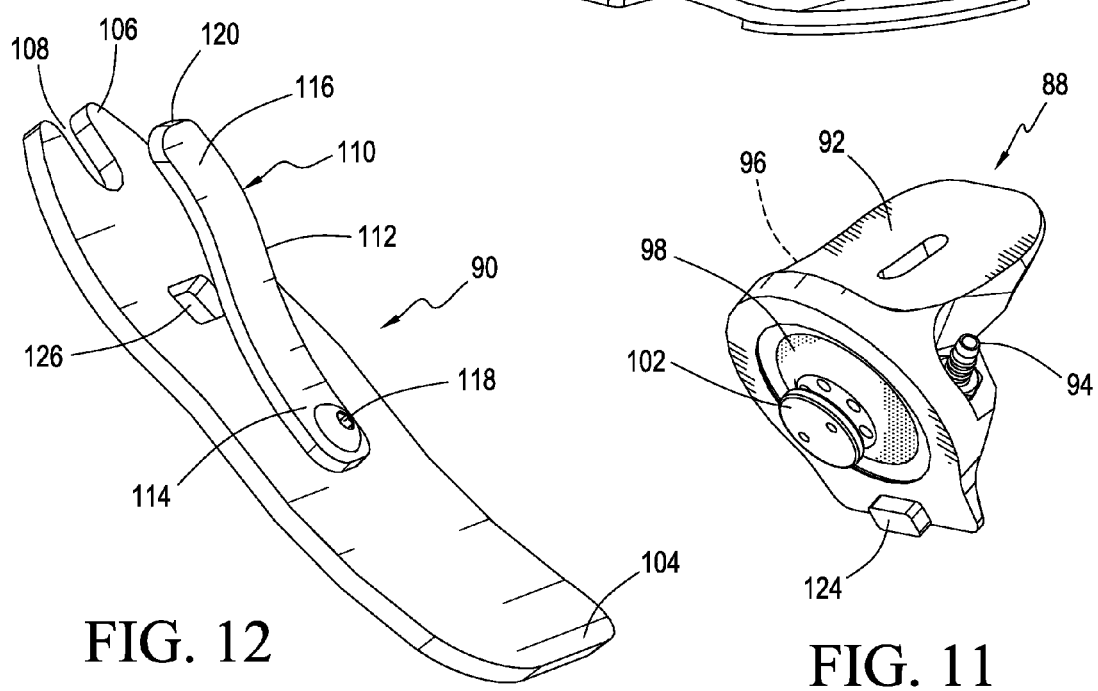
FIG. 12
FIG. 11

PUMP MECHANISM

TECHNICAL FIELD

The disclosure relates to the field of prosthetic devices, and more particularly to a prosthetic device, system and pump mechanism for increasing vacuum in a vacuum assisted suspension system.

BACKGROUND

An ongoing challenge in the development of prosthetic devices is the attachment of the prosthetic device to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb (or a liner donned on the limb) and a socket or receptacle coupled to the prosthetic limb. Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. However, in utilizing the motion of the user, known pumps rely on complete compression of the pump to expel air from the pump before the pump can be decompressed to generate the vacuum. Because the impact and displacement of the pump is not consistent and varies between users, the vacuum and thus attachment between residual limb and the socket can be unpredictable and/or inadequate, causing the user discomfort, grief and even injury.

Different attempts have been made to design a more efficient pump. For instance, U.S. Pat. No. 9,072,617 (commonly owned by assignee) describes a membrane pump system including a frame component and a support blade component, with a flexible membrane between them. The support blade component is attached to prosthetic foot near the ankle, while the frame component sits on a heel pad. The frame and support blade components are fixed to each other where they coincide close to the middle of the foot. The frame and blade components are designed so that when weight is placed on the heel of the prosthetic foot the frame component moves upward and the support blade components moves downwards, thus pulling and expanding the membrane between them. Accordingly, the membrane pump mechanism is located between the two frame components. When the membrane expands, air is efficiently drawn from the socket.

While the membrane pump system described in U.S. Pat. No. 9,072,617 tends to generate a more efficient vacuum, the frame and support blade components add bulk and weight to the prosthetic limb, imposing a greater burden on the user when walking. Furthermore, the arrangement of the frame and support blade components in relation to each other and the foot can affect the functionality of the foot. In addition, the membrane pump system must engage the heel of the prosthetic foot to generate a vacuum, limiting its versatility.

There is a need for a prosthetic device, system, and pump mechanism that provides freedom of vacuum suspension for a prosthetic system. There is also a call for a prosthetic device that provides a secure vacuum without losing suction and confidence to the user over a period of use. It is also desirable for prosthetic devices to draw a vacuum while being lightweight, streamlined, and versatile.

SUMMARY

Embodiments of the prosthetic system provide vacuum assisted suspension by generating negative pressure inside a prosthetic socket worn over a residual limb, and reducing sliding movement between the liner and the socket. The function of the embodiments is automatic as it is activated during gait. The weight placed on the foot member of the prosthetic foot expands and compresses the foot member, which, in turn, expands a pump mechanism positioned between the end sections of the foot member that efficiently draws air out from the socket in each step, and expels it into the atmosphere during swing phase as the pump mechanism returns to an original configuration.

The pump mechanism utilizes the action of the prosthetic foot to create negative pressure inside the socket without substantially affecting the functionality of the prosthetic foot. It also does so without the use of complicated and bulky components as in the prior art, resulting in more secure and reliable elevated vacuum suspension. Furthermore, the pump mechanism can be a separate add-on module to the prosthetic foot and can be adapted to fit a number of different prosthetic feet, providing versatility.

According to an embodiment, the prosthetic system includes a prosthetic foot with a foot member defining a first end portion, a second end portion, and an intermediate portion defining a curvature and extending between the first and second end portions. A pump mechanism is coupled to the foot member. The pump mechanism includes a housing s defining a cavity, and a membrane situated in the cavity. The pump mechanism is movable between an original configuration in which the volume of a fluid chamber defined between the membrane and a bottom of the cavity is zero or near-zero, and an expanded configuration in which the volume of the fluid chamber is increased. A movable member includes a first portion coupled to the membrane and a second portion arranged to slidably engage the foot member.

Relative movement between the first and second end portions can move the first portion of the movable member relative to the housing and slide the second portion along a length of the foot member to shift the pump mechanism between the original and expanded configurations. For instance, as the prosthetic foot moves through mid-stance and/or toe-off, the first and second ends portions of the foot member can flex or move toward one another from a resting position, causing the foot member to apply an upward force on the second portion of the movable member. This upward force on the second portion of the movable member can force the second portion to slide along a length of the foot member and pivot and/or flex the movable member around an edge of the housing, which, in turn, moves the first portion of the movable member away from the housing. This pulls the membrane away from the housing moving the pump mechanism to the expanded configuration.

The increase in volume of the fluid chamber creates a vacuum in the pump mechanism. Compression of the prosthetic foot thus automatically creates a vacuum in the pump mechanism without the use of fixed frame and support blade components that add detrimental weight and bulk to the prosthetic foot as in the prior art. It also can do so without engaging the heel of the prosthetic foot, increasing its versatility.

At the end of the stance phase or when the weight of the user is removed from the prosthetic foot, the prosthetic foot returns to its resting position. The inherent properties of the material of the movable member can help return the movable member to its un-flexed state, moving the pump mechanism back toward its original configuration and decreasing the volume of the fluid chamber to a zero or near zero volume. During the return of the membrane toward the housing, the pump mechanism expels fluid in the fluid chamber out of the pump mechanism. Because the pump mechanism returns to its original configuration of zero or near-zero volume in the fluid chamber at the beginning or end of each gait cycle, all fluid drawn into the pump mechanism is automatically expelled.

Because the second portion of the movable member can slide or move along a length of the foot member during gait, the movable member exerts less resistance to the normal action of the prosthetic foot than the frame and support members in the prior art. In addition, the simplified and lightweight design of the pump mechanism and the movable member reduces the overall weight and bulk of the prosthetic foot during gait.

According to a variation, the movable member can be easily and quickly removed from the pump mechanism without the use of tools. For instance, the movable member can include a clip mechanism arranged to selectively clip the movable member on the housing of the pump mechanism.

According to a variation, the pump mechanism can be a separate add-on module to the prosthetic foot and can be adapted to fit a number of different prosthetic feet. For instance, the pump mechanism can be removably attached to the adaptor via a single fastener and the movable member can slidably engage with the foot member during compression and expansion of the foot member.

BRIEF DESCRIPTION OF THE DRAWINGS

These and other features, aspects, and advantages of the present disclosure will become better understood regarding the following description, appended claims, and accompanying drawings.

FIG. 1 shows a prosthetic device with a pump mechanism according to an embodiment.

FIG. 2 shows a front view of the prosthetic device in FIG. 1.

FIG. 10 shows a prosthetic device with a pump mechanism according to another embodiment.

FIG. 11 shows the pump mechanism in FIG. 10 removed from the prosthetic device for ease of reference.

FIG. 12 shows the movable member in FIG. 10 removed from the prosthetic device for ease of reference.

DETAILED DESCRIPTION OF THE DISCLOSURE

Figures 3, 4:
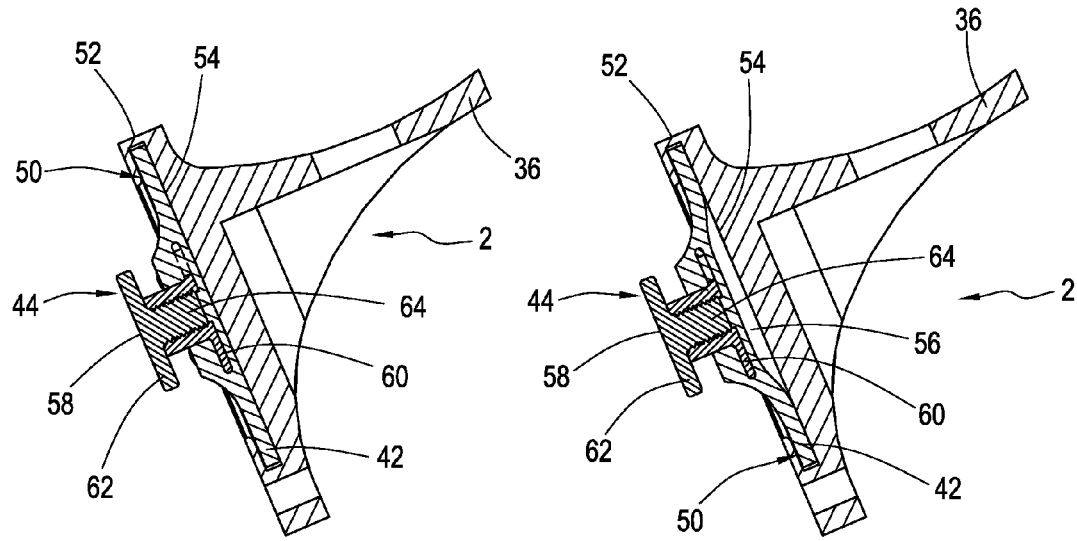
FIG. 3 shows a sectional view of the pump mechanism in FIG. 1 in a first configuration.
FIG. 4 shows a sectional view of the pump mechanism in FIG. 1 in a second configuration.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The embodiments of a prosthetic device will be described which form part of a vacuum system. A vacuum pump mechanism having a fluid connection with a socket assists in creating a vacuum between a residual limb and the socket by pumping fluid out of the socket. The fluid is pumped out of the socket when the user puts his weight on a prosthetic foot such as upon heel strike, mid-stance and/or toe-off. The user's weight on the prosthetic foot can cause the pump mechanism to increase the volume of a fluid chamber in the pump mechanism. The increase in volume of the pump mechanism draws in fluid from the vacuum space between the residual limb and the socket of a prosthetic limb. In this manner, the pump mechanism decreases the air pressure within the vacuum space causing a vacuum effect.

After the weight is removed, and/or shifted on the prosthetic foot, the volume of the fluid chamber in the pump mechanism is automatically decreased. The connection between the vacuum space and the pump may have a one-way valve assembly, so all of the air within the volume of the pump is expelled out of an outlet to another space or to atmosphere. The outlet is provided with a one-way valve assembly so the vacuum space is the only source of air.

The vacuum suspension system of the present disclosure produces a vacuum effect in a prosthetic socket that is advantageous over prior art devices that require compression of the pump to expel air before the pump can be decompressed to draw in air. The present disclosure also achieves smaller fluctuations in air pressure than the prior art systems, so the difference between the greatest pressure and lowest pressure in the vacuum space of the socket is less.

The efficiency of the pump mechanism is determined at least in part by how effectively the volume of the fluid chamber is reduced. Since the pump mechanism begins at and returns to the original state of zero or near-zero volume at the beginning or end of each cycle in some embodiments, the volume of the fluid chamber is determined by the force applied to the pump, not by a full compression and recompression cycle as in the prior art. In addition, all fluid drawn into the pump mechanism is expelled afterwards, fully utilizing the volume of the fluid chamber.

The vacuum suspension system also reduces volume fluctuations of the residual limb and allows for increased proprioception and reduced pistoning since there is a better attachment between the socket and the residual limb. It may also be beneficial to produce hypobaric pressure below a certain level in the socket. This may be achieved using a sealing membrane or seal component between the residual limb and the socket, instead of the conventional sealing method of using a sleeve to form an airtight connection between the residual limb and the proximal end of the socket. The sealing membrane may be on a prosthetic liner as described in U.S. Pat. Nos. 8,034,120; 8,097,043; and 9,066,821, each incorporated by reference and belonging to the assignee of this disclosure.

The benefit of using a liner having a seal or seal component reduces the volume of air to be drawn out of the socket and therefore, a better suspension may be achieved in a shorter time period. Using a silicone liner with integrated seal also provides the added benefit that the hypobaric region is not directly applied to the skin.

The vacuum pump mechanisms in the embodiments of the prosthetic device described are generally described as a pump mechanism and may include any suitable type of pump mechanism. For instance, the pump mechanism may be a pump as described in U.S. Pat. Nos. 9,044,348 and 9,072,617, each incorporated by reference and belonging to the assignee of this disclosure. A piston-type pump may be used in the embodiments in place of a membrane-type pump. A bladder-type pump may also be used in the embodiments in place of a membrane-type pump, and a skilled person would understand that the pump mechanisms described may also be used with a bladder-type pump and vice versa.

A bladder-type pump has an interior fluid chamber surrounded by an airtight material. When the interior chamber is expanded, the opposing walls are moved away from each other by extending at least one side wall of the pump. The side walls of the bladder-type pump may have an accordion-like shape or be formed of a polymeric material which allow for the increase in distance between the opposing walls.

A membrane-type pump has at least one wall of flexible material and a second opposing wall which may be rigid or flexible. The edges of the two walls are attached to each other such that when a force applies to the pump to expand the interior fluid chamber, the force deforms at least the flexible wall, and the flexible wall arcs outward to form an interior fluid chamber. To allow for deformation, the flexible wall may be made of a polymeric material including elastomeric material such as rubber or plastic.

The bladder-type pump and membrane-type pump are arranged so that when no force applies to the pump or no weight is placed on the prosthetic device the volume of the interior fluid chamber is zero or near-zero. The pumps described and shown have a cylindrical shape. A skilled person would understand that the pumps may have a variety of shapes, for example, a diamond, rectangular, or triangular shape.

The specific embodiments of the prosthetic device will now be described regarding the figures.

First Embodiment of the Prosthetic Device

FIGS. 1-9 show a first embodiment of the prosthetic device 1 comprising a pump mechanism 2 and a prosthetic foot 4 with dual foot blades. As seen in FIGS. 1 and 2, the prosthetic foot 4 has an upper foot member 6 that extends from a first end portion 8 terminating at a first or posterior end to a second end portion 10 terminating at a second or anterior end. The first end portion 8 can be generally horizontally oriented, and the second end portion 10 can be generally horizontally oriented.

The upper foot member 6 can have an intermediate portion 12 extending between the first end portion 8 and the second end portion 10. The intermediate portion 12 can have a flexible configuration and can define a curvature. The intermediate portion 12 can be generally forwardly-facing concave so that the upper foot member 6 is generally C-shaped. The intermediate portion 12 and/or the first end portion 8 can be generally at a location of a natural human ankle.

The prosthetic foot 4 can include a lower foot member 14, which is disposed generally below the upper foot member 6. The lower foot member 14 can extend from a first end portion 16 terminating at a first end to a second end portion 18 terminating at a second end. The first end portion 16 can be generally horizontally oriented, and the second end portion 18 can be generally horizontally oriented. The lower foot member 14 can define an intermediate portion 20 between the first end portion 16 and the second end portion 18. The intermediate portion 20 can have a flexible configuration and can define a curvature. The intermediate portion 20 can be generally forwardly-facing concave so that the lower foot member 14 is generally C-shaped.

The prosthetic foot 4 can have a heel member 22 that extends rearwardly from a first or posterior end 24 to a free second or posterior end 26 and is disposed below at least a portion of the lower foot member 14. The heel member 22 can have a curvilinear profile along its length.

In the illustrated embodiment, the upper foot member 6 and the lower foot member 14 extend generally parallel to each other and have generally the same shape. Intermediate portions 12, 20 of the upper 6 and lower 14 foot members can have predetermined lengths to provide the foot with a desired flexibility. As seen, the second end of the lower foot member 14 extends beyond the second end of the upper foot member 6. The upper foot member 6 is coupled to the lower foot member 14 and heel member 22 at the second end portion 18 of the upper foot member 6 via fasteners 28.

An adaptor 30 can be coupled to the upper foot member 6 and the lower foot member 14. The adaptor 30 can include a cavity sized and shaped to receive an attachment portion of the prosthetic foot 4, such as the posterior or first ends of the lower and upper foot members 14, 6. The adaptor 30 can include a generally horizontal, rearwardly-facing cavity.

In use, the prosthetic foot 4 can expand and compress through flexion of the foot members 6, 14. The prosthetic foot 4 is in expansion when the first and second end portions of the foot members 6, 14 are moved or flexed apart from a resting position of the foot 4, increasing the distance between the first and second end portions of the upper and lower foot members 6, 14. The prosthetic foot 4 is in compression when the first and second end portions of the foot members 6, 14 are moved or flexed toward one another from the resting position of the foot, reducing the distance between the first and second end portions of the foot members 6, 14.

Different examples of the prosthetic foot 4 are described in greater detail in U.S. Pat. No. 9,017,421, issued on Apr. 28, 2015. This disclosure is incorporated by reference and belongs to the assignee of this disclosure.

In order to better understand the operation of the prosthetic foot 4, a basic discussion of the gait cycle is required. The gait cycle defines the movement of the leg between successive heel contacts of the same foot. The gait cycle has two phases: stance and swing. Of particular interest is the stance phase which generally includes heel-strike or initial contact, mid-stance, and toe-off.

It is during the stance phase that the mechanics of a prosthetic foot 4 come into play. Upon heel strike, the prosthetic foot 4 is in expansion, providing cushioning to the user. During mid-stance, at which time the weight of the user is transmitted through the prosthetic foot 4 to a supporting surface, the prosthetic foot 4 moves from expansion into compression. The prosthetic foot 4 remains in compression through toe-off until the weight of the user is removed from the prosthetic foot, at which time the prosthetic foot 4 returns to its resting position.

The pump mechanism 2 can be coupled to the prosthetic foot 4 at any suitable location but is shown coupled to the adaptor 30 located on the posterior or first ends of the lower and upper foot members 14, 6. The pump mechanism 2 can be made generally from carbon fiber and an elastomeric compound (e.g., a membrane) providing durable yet lightweight components. The prior art pump mechanisms are of heavy metal construction, which imposes a significant weight burden on the user when walking.

The pump mechanism 2 is located between the adaptor 30 and a movable member 34 engaging the upper foot member 6. As described in more detail below, movement of the movable member 34 can move or shift the pump mechanism 2 between the original configuration and the expanded configuration.

The pump mechanism 2 includes a housing 36 containing two valve assemblies 38, 40, a membrane 42 (shown in FIGS. 3 and 4), and a connector 44 (shown in FIGS. 3 and 4). The valve assemblies can include a one-way valve, also referred to as a check valve. A preferred type of one-way valve used is a duckbill valve. It should be appreciated however that other types of one-way valves are possible.

Figure 7:
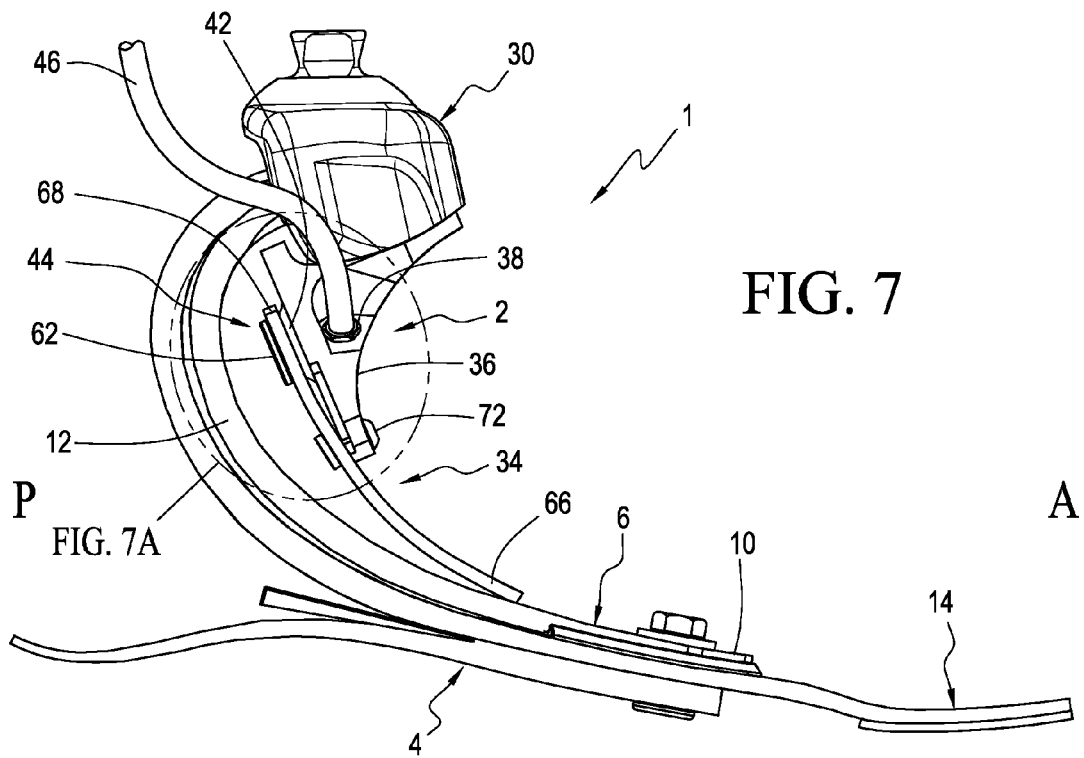
FIG. 7 shows a side view of the prosthetic device in FIG. 1 in a first position.
Figure 7A:
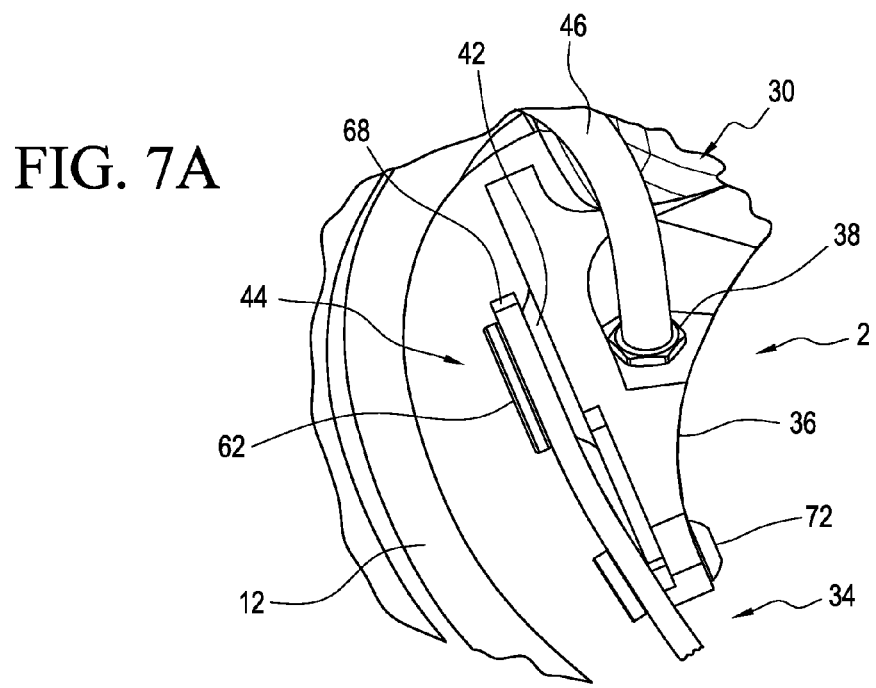
FIG. 7A shows a side view corresponding to detail 7A in FIG. 7.
Figure 8:
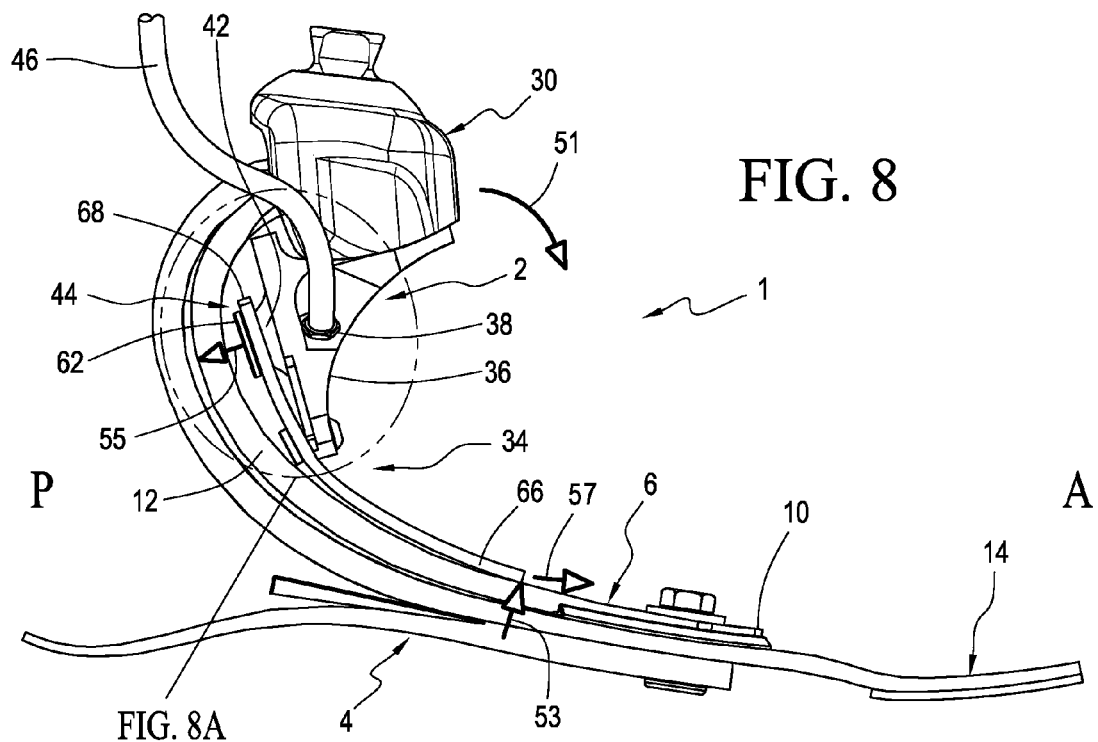
FIG. 8 shows a side view of the prosthetic device in FIG. 1 in a second position.
Figure 8A:
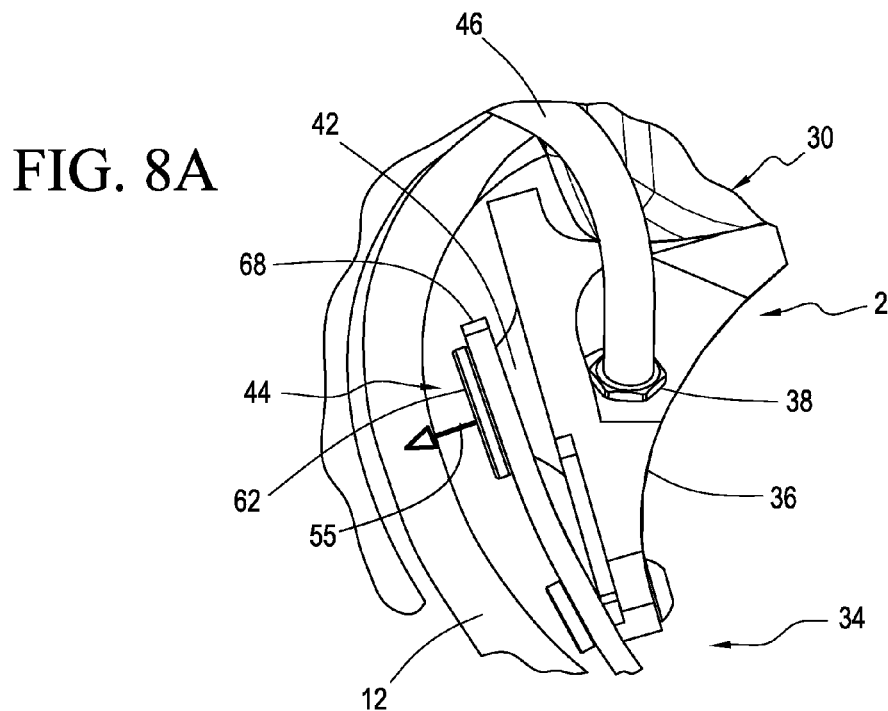
FIG. 8A shows a side view corresponding to detail 8A in FIG. 8.

The valve assembly 38 is arranged to only allow fluid to enter the pump mechanism 2 and can be connected to a tube 46 (shown in FIGS. 7 and 8). Through the tube 46, the pump mechanism 2 can be in fluid communication with the cavity of a prosthetic socket. When the volume of the pump mechanism 2 increases, fluid (e.g., air) can be drawn out from the socket via the valve assembly 38. The valve assembly 40 is arranged to only allow fluid to be expelled out of the pump mechanism 2, preferably to atmosphere.

The housing 36 can be coupled to the adaptor 30 via at least one fastener 48. An upper surface of the housing 36 can generally complement the lower surface of the adaptor 30. It should be appreciated that the pump mechanism 2 can be a separate add-on module to the prosthetic foot 4. For instance, the pump mechanism 2 can be removably coupled to the adaptor 30 via the fastener 48 and to the movable member 34 via the connector 44. Because the pump mechanism 2 is not integrated into the prosthetic foot 4, failure of the pump mechanism 2 advantageously would not affect the performance of the prosthetic foot 4. The housing 36 can have a rigid configuration.

Figure 5:
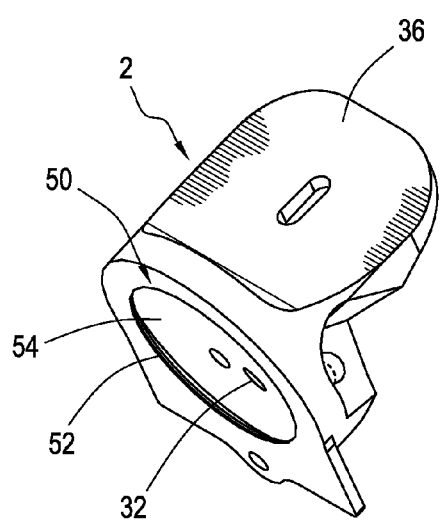
FIG. 5 shows a schematic view of the pump mechanism in FIG. 1 removed from the prosthetic device for ease of reference.

Referring to FIGS. 3-5, the bottom surface of the housing 36 defines a cavity 50 that is provided with an undercut circumferential groove 52 between an open end of the cavity 50 and a closed bottom 54 of the cavity 50. An outer radial edge portion of the membrane 42 can be situated in the circumferential groove 52 such that a seal is formed between the membrane 42 and the housing 36. Optionally, an adhesive can be applied between the housing 36 and the outer radial edge portion of the membrane 42, increasing the sealing effect. The bottom 54 of the cavity 50 has two openings 32 (shown in FIG. 5) which extend into the housing 36 to form internal passageways providing fluid communication between a fluid chamber defined below and the one-way valve assemblies 38, 40.

The pump mechanism 2 is movable between an original configuration (shown in FIG. 3) in which the volume of a fluid chamber 56 defined between the top surface of the membrane 42 and the bottom 54 of the cavity is zero or near-zero, and an expanded configuration (shown in FIG. 4) in which the volume of the fluid chamber 56 is increased.

As seen, the bottom 54 of the cavity 50 substantially complements the top surface of the membrane 42 such that when no force is exerted on the pump mechanism 2 it is in the original configuration. Both the bottom 54 of the cavity 50 and the top surface of the membrane 42 can be generally flat.

When a force is exerted on the membrane 42 in a direction away from the housing 36, the pump mechanism 2 moves toward the expanded configuration as the force pulls a portion of the membrane 42 away from the bottom 54 of the cavity 50, causing deformation of the membrane 42 and an increase in volume of the fluid chamber 56. This increase in volume of the fluid chamber 56 can draw fluid into the fluid chamber 56 from the socket through the one-way valve assembly 38. The housing 36 may be formed of metal such as stainless steel, carbon fiber, or plastic or any other material which would provide sufficient strength to resist deformation when pulled away from the membrane 42.

Once the force is removed from the membrane 42, the pump mechanism 2 returns toward its original configuration as the membrane 42 returns toward the bottom 54 of the cavity 50 and fluid within the fluid chamber 56 is expelled out of the one-way valve assembly 40. The membrane 42 can be elastomeric and can use at least in part its material properties to naturally or elastically return to its original position on the bottom 54 of the cavity 50.

The membrane 42 may have any desired shape, but is shown having a generally circular or elliptical shape. The membrane 42 can be attached at or near its center point to the movable member 34 while the outer radial edge portion of the membrane 42 is attached to the housing 36 such that when the membrane 42 is pulled away from the housing 36 a pocket forms in a middle area of the membrane 42 due to the deformation of the membrane 42. The formation of the pocket increases the volume of the fluid chamber 56. The pump mechanism 2 thus uses a compliant membrane to create suction.

The connector 44 can be an insert 58 having an upper radial flange 60 embedded in the membrane 42, a lower radial flange 62 below the membrane 42, and a shaft portion 64 extending between the upper flange 60 and the lower flange 62. In some embodiments, the insert 58 may be of a two-piece construction such that the lower flange 62 can be threadedly removed from the upper flange 60 embedded in the membrane 42. The insert 58 may be formed of metal, plastic, or any suitable other material. In other embodiments, the upper flange 60 of the insert 58 may extend substantially into the membrane 42 or may be formed of a material that is part of the membrane 42 (e.g. a flexible metal member).

Figure 6:
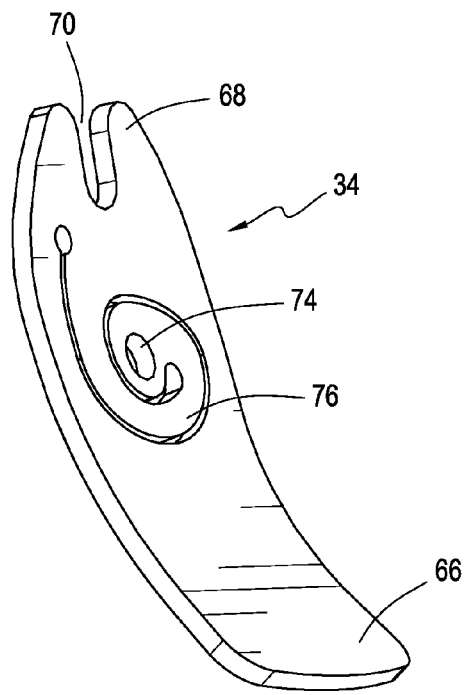
FIG. 6 shows a schematic view of the movable member in FIG. 1 removed from the prosthetic device for ease of reference.

As seen in FIGS. 6-8, the movable member 34 is a plate including a first portion or posterior end portion 68 and a second portion or an anterior end portion 66. The anterior end portion 66 is arranged to engage the upper side or dorsal aspect of the prosthetic foot 4 (e.g., the upper foot member 6). The anterior end portion 66 can engage the intermediate portion 12 or the second end portion 10 of the upper foot member 6. The posterior end portion 68 is arranged to connect to the membrane 42 via the connector 44. The movable member 34 can have a flexible, rigid, and/or semi-rigid configuration.

The movable member 34 extends at an angle between the upper foot member 6 and the membrane 42. A clearance can be formed between the movable member 34 and the upper foot member 6. Near the pump mechanism 2, the clearance is greater so that the upper foot member 6 does not impede movement of the posterior end portion 68 of the movable member 34.

The movable member 34 can define a slot 70 in a terminal edge of the posterior end portion 68 that extends along a portion of the length of the movable member 34. To attach the movable member 34 to the membrane 42, the shaft portion 64 of the insert 58 can be slid into the slot 70 such that the posterior end portion 68 of the movable member 34 is located between the bottom surface of the membrane 42 and the lower flange 62 of the insert 58. Through the structure of the connector 44 and the movable member 34, the movable member 34 has the benefit of being easily and quickly removed and/or replaced from the prosthetic foot 4.

The movable member 34 is connected to the housing 36 at or near an anterior edge portion of the housing 36. The movable member 34 can be connected to the housing 36 in any suitable manner but is shown attached to the housing 36 via a fastener 72. The movable member 34 can define an aperture 74 for receiving the fastener 72 to connect the movable member 34 to the housing 36.

As best seen in FIG. 6, the movable member 34 defines an internal slot 76 spiraling around the aperture 74. This has the effect of providing additional flexibility to the movable member or a spring force that can at least in part help move the pump mechanism 2 back toward its original configuration after toe-off as discussed below. The location, shape, and/or length of the internal slot 76 can be adjusted based on the flexibility of the prosthetic foot 4 during gait, the size of the prosthetic foot 4, the weight of the user, and/or other factors.

FIG. 7 shows the prosthetic foot 4 in its resting position. The anterior direction is generally indicated by the reference A and the posterior direction is generally indicated by the reference P. When the prosthetic foot 4 is in the resting position, the anterior end portion 66 of the movable member 34 is engaged with the dorsal aspect of the upper foot member 6 and the pump mechanism 2 is in its original configuration. Upon heel strike, the prosthetic foot 4 moves into expansion, which, in turn, lifts or slides the anterior end portion 66 of the movable member 34 in the posterior direction P along a length of the prosthetic foot 4 or the upper foot member 6. With the prosthetic foot 4 in expansion, the pump mechanism 2 remains in its original configuration.

As the prosthetic foot 4 moves from heel strike through mid-stance and/or toe-off, the prosthetic foot 4 moves into compression as seen in FIG. 8. In compression, the first and second end portions of the foot members 6, 14 move or bend toward one another as generally indicated by arrow 51, causing the anterior edge of the housing 36 to apply a downward force on the upper surface of the movable member 34 and the intermediate portion 12 of the upper foot member 6 to apply an upward force (as generally indicated by arrow 53) on the lower surface of the anterior end portion 66 of the movable member 34. In response to these forces on the movable member 34, the anterior end portion 66 of the movable member 34 can slide or move in the anterior direction A along a length of the prosthetic foot 4 or upper foot member 6 as generally indicated by arrow 57.

In addition, the upward force on the anterior end portion 66 of the movable member 34 from the upper foot member 6 and the downward force on the movable member 34 from the housing 36 cause the movable member 34 to pivot and/or flex around the anterior edge of the housing 36, which, in turn, moves the posterior end portion 68 of the movable member 34 downwardly away from the housing 36 as generally indicated by arrow 55. This pulls the membrane 42 away from the housing 36, moving the pump mechanism 2 to the expanded configuration. More particularly, the posterior end portion 68 pulls the membrane 42 away from the housing 36 to deform the membrane 42 between the movable member 34 and the housing 36, increasing the volume of the fluid chamber 56.

This increase in volume of the fluid chamber 56 creates a vacuum in the pump mechanism 2, pulling fluid into the pump mechanism 2 through the one-way valve assembly 38. Compression of the prosthetic foot 4 thus automatically creates a vacuum in the pump mechanism 2. This is advantageous over prior art prosthetic devices that require compression of the pump to expel air before the pump can be decompressed to draw in air. Further, because the pump mechanism 2 does not need to be first compressed before it can create a vacuum upon decompression, the pump mechanism 2 can achieve smaller fluctuations in air pressure than the prior art devices, so the difference between the greatest pressure and lowest pressure in the vacuum space of the socket is less than compared to the prior art devices.

It should be appreciated that the connector 44 can slide within the slot 70 as the posterior end portion 68 moves away from the housing 36. This advantageously allows the posterior end portion 68 to travel along an arcuate path as the movable member 34 pivots or flexes about the anterior edge of the housing 36.

At the end of the stance phase or when the weight of the user is removed from the prosthetic foot 4, the prosthetic foot 4 returns to its resting position and the inherent properties of the material of the movable member 34 can help return the movable member 34 to its un-flexed state, moving the pump mechanism 2 back toward its original configuration and decreasing the volume of the fluid chamber 56 to a zero or near zero volume.

During the return of the membrane 42 toward the housing 36, the pump mechanism 2 expels fluid in the fluid chamber 56 out of the one-way valve assembly 40. Because the pump mechanism 2 returns to its original configuration of zero or near-zero volume in the fluid chamber 56 at the beginning or end of each gait cycle, all fluid drawn into the pump mechanism 2 is automatically expelled. This is advantageous because prior art devices rely on complete compression of the pump in expelling air in each gait cycle to use the pump to its maximum capacity. It is difficult for complete compression to occur in every cycle using the gait of a user as the actuating force since the impact and displacement of the pump is not consistent and varies between users.

To meet the stiffness/flexibility, strength, and weight requirements needed for use on the prosthetic foot, the movable member 34 can be made of a durable but flexible material such as carbon fiber cloth, unidirectional composites, plastic, or metal. The length, curvature, and/or shape of the movable member 34 can be adjusted based on the flexibility of the prosthetic foot 4 during gait, the length of the prosthetic foot 4, the weight of the user, and/or other factors.

Figure 9:
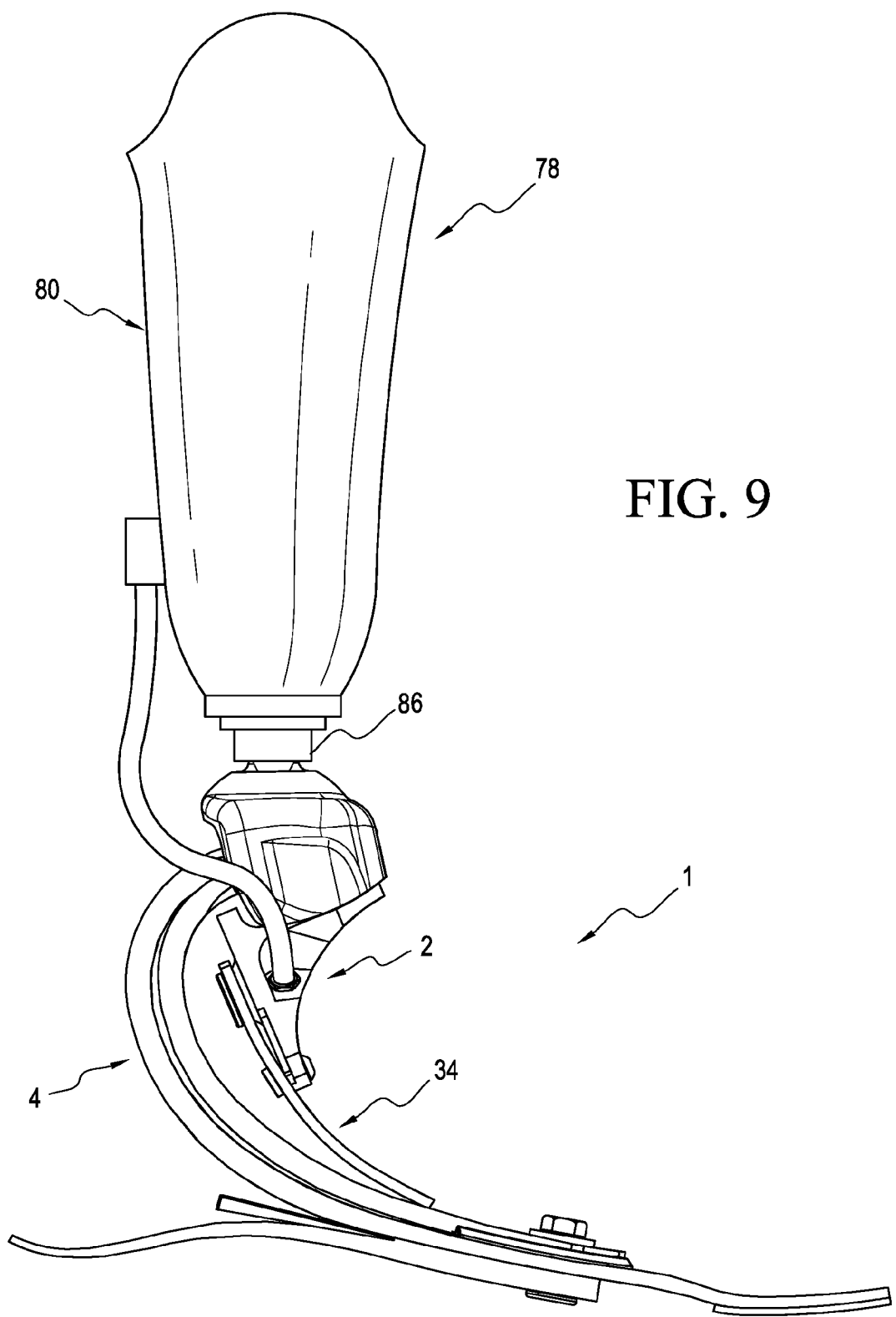
FIG. 9 shows a schematic view of a prosthetic system according to an embodiment.

FIG. 9 illustrates a vacuum suspension system 78 including the prosthetic device 1 having the pump mechanism 2 and the prosthetic foot 4. The vacuum suspension system 78 has a socket 80, a liner preferably including a seal component, a valve assembly 82, a tube 84, connecting the pump mechanism 2 to the socket 80, and the prosthetic foot 4. The socket 80 defines an interior space, and interior wall delimiting the interior space. The vacuum suspension system 78 may also employ an adaptor system 86. Alternatively, the adaptor system 86 can be replaced with a shock and/or rotation module.

The vacuum suspension system 78 provides improved proprioception and volume control since there is better attachment between the socket 80 and the residual limb. The vacuum suspension system 78 includes the pump mechanism 2 and movable member 34, as described above, which provide a vacuum assisted suspension by generating a negative pressure (vacuum) inside the socket 80. The function of the vacuum suspension system 78 can be fully automatic. During mid-stance and/or toe-off, compression of the prosthetic foot 4 expands the pump mechanism 2 to efficiently draw fluid out of the socket in each step. During the swing phase, decompression of the prosthetic foot 4 permits the pump mechanism 2 to return to its original position, expelling the fluid drawn from the socket 80 to atmosphere. The pump mechanism 2 thus can create a negative pressure inside the socket 80, resulting in a secure and reliable elevated vacuum suspension that provides an intimate suspension as the negative pressure formed inside of the socket 80 holds the liner and the residuum firmly to the socket wall.

Second Embodiment of the Prosthetic Device

A second embodiment of a prosthetic device 3 is shown in FIGS. 10-12. This embodiment can be similar to the first embodiment illustrated in FIGS. 1-9 except that the movable member is attached to the pump mechanism via clip mechanism described below. As seen in FIG. 10, the prosthetic device 3 includes the prosthetic foot 4 and a pump mechanism 88 coupled to the adaptor 30 of the prosthetic foot 4. The pump mechanism 88 is operable between the adaptor 30 and a movable member 90 operably coupled to the pump mechanism 88 and arranged to slidably engage the dorsal aspect of the prosthetic foot 4 or upper foot member 6.

As seen in FIG. 11, the pump mechanism 88 includes a housing 92 containing two one-way valve assemblies 94, 96, a membrane 98, and a connector 102. The valve assembly 94 only allows fluid to enter the pump mechanism 88 which can be in fluid communication with the cavity of a socket. The valve assembly 96 only allows fluid to be expelled out of the pump mechanism 88, preferably to atmosphere. The connector 102 includes an upper radial flange embedded in the membrane 98, a lower radial flange below the membrane 98, and a shaft portion extending between the upper and lower flange.

Similar to the pump mechanism 2, the pump mechanism 88 relies upon deformation of the membrane 98 to move between an original configuration in which the volume of a fluid chamber defined between the top surface of the membrane 98 and the bottom of the housing 92 is zero or near-zero, and an expanded configuration in which the volume of the fluid chamber is increased. The housing 92 is arranged to surround the outer radial edge portion of the membrane 98 and creates a seal with the membrane 98. The bottom surface of the housing 92 defines a pair of openings which extend into the housing 92 to form internal passageways to provide fluid communication between the fluid chamber and the two one-way valve assemblies 94, 96.

As seen in FIG. 12, the movable member 90 is an elongated plate having a first portion or posterior end portion 106 and a second portion or an anterior end portion 104. The anterior end portion 104 is arranged to engage the dorsal aspect of the prosthetic foot 4 (e.g., upper foot member 106) and the posterior end portion 106 is coupled to the membrane 98 via the connector 102. The movable member 90 can have a flexible, rigid, and/or semi-rigid configuration.

A slot or notch 108 is formed in the terminal edge of the posterior end portion 106. The connector 102 can be slidably received within the notch 108 such that a portion of the movable member 90 is located between the bottom surface of the membrane 98 and the lower flange of the connector 102, securing the movable member 90 to the membrane 98.

The movable member 90 is removably attached to the housing 92 via a clip mechanism 110. The clip mechanism 110 includes a main body 112 having an anterior end section 114, a posterior end section 116, and a curvilinear profile along its length. The anterior end section 114 can be attached to the movable member 90 via a fastener 118 and the posterior end section 116 is arranged to engage the upper surface of the housing 92 when the movable member 90 is clipped to the housing 92. The posterior end section 116 is formed so as to bias the clip mechanism 110 toward the upper surface of the movable member 90, whereby the housing 92 can be secured between the lower surface of the posterior end section 116 and the upper surface of the movable member 90.

Through the structure of the clip mechanism 110 and the movable member 90, the movable member 90 has the benefit of being easily and quickly removed from the pump mechanism 88 without the use of tools. The clip mechanism 110 can be made of a durable but flexible material such as carbon fiber cloth, unidirectional composites, plastic, or metal. The length, curvature, and/or shape of the clip mechanism 110 can be adjusted based on the flexibility of the movable member 90 during gait, the length of the movable member 90, and/or other factors.

Optionally, a posterior edge 120 of the posterior end section 116 of the clip mechanism 110 can be angled or curved upward. This can create an axis other than the posterior edge about which the clip mechanism 110 can pivot on the housing 92 as the user walks on the prosthetic foot 4.

The upper surface of the housing 92 defines a seat 122 (best shown in FIG. 10) arranged to accommodate the posterior end section 116 of the clip mechanism 110 when the movable member 90 is clipped to the housing 92. This beneficially limits or prevents the clip mechanism 110 from sliding sideways off of the housing 92.

A raised piece 124 can be formed on the lower surface of the housing 92. When the movable member 90 is clipped to the housing 92, the raised piece 124 can extend into a corresponding opening 126 defined in the movable member 90, helping to position and secure the movable member 90 on the housing 92.

Upon mid-stance and/or toe-off, the prosthetic foot 4 moves into compression. In compression, the first and second end portions of the foot members 6, 14 move toward one another causing an anterior edge of the housing 92 to apply a downward force on the upper surface of the movable member 90 and the dorsal aspect of the upper foot member 6 to apply an upward force on the lower surface of the anterior end portion 104 of the movable member 90.

The upward force on the lower surface of the anterior end portion 104 of the movable member 90 causes the movable member 90 to pivot and/or flex around the anterior edge of the housing 92, which, in turn, moves the posterior end portion 106 of the movable member 90 away from the housing 92. As the posterior end portion 106 moves downwardly away from the housing 92, the clip mechanism 110 flexes as it is forced away from the movable member 90.

The movement of the posterior end portion 106 away from the housing 92 moves the pump mechanism 88 to the expanded configuration, increasing the volume of the fluid chamber to create a vacuum in the pump mechanism 88 and to pull fluid into the pump mechanism 88 through the one-way valve assembly 94.

At the end of the stance phase or when the weight of the user is removed from the prosthetic foot 4, the prosthetic foot 4 returns to its resting position and the properties of the material of the clip mechanism 110 can help return the posterior end portion 106 of the movable member 90 toward the housing 92, moving the pump mechanism 88 back toward its original configuration and decreasing the volume of the fluid chamber to a zero or near zero volume. During the return of the pump mechanism 88 toward its original configuration, the pump mechanism 88 expels fluid in the fluid chamber out the one-way valve assembly 96.

Third Embodiment of the Prosthetic Device

Figure 13A:
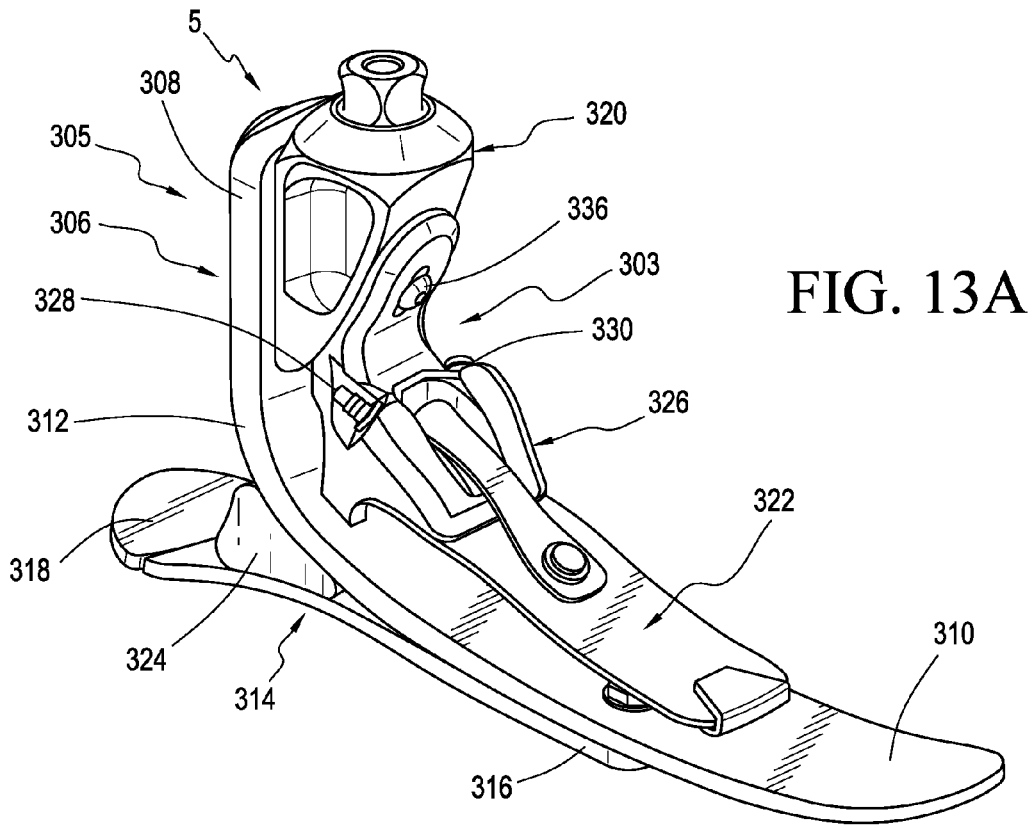
FIG. 13A shows a prosthetic device with a pump mechanism according to another embodiment.
Figure 13B:
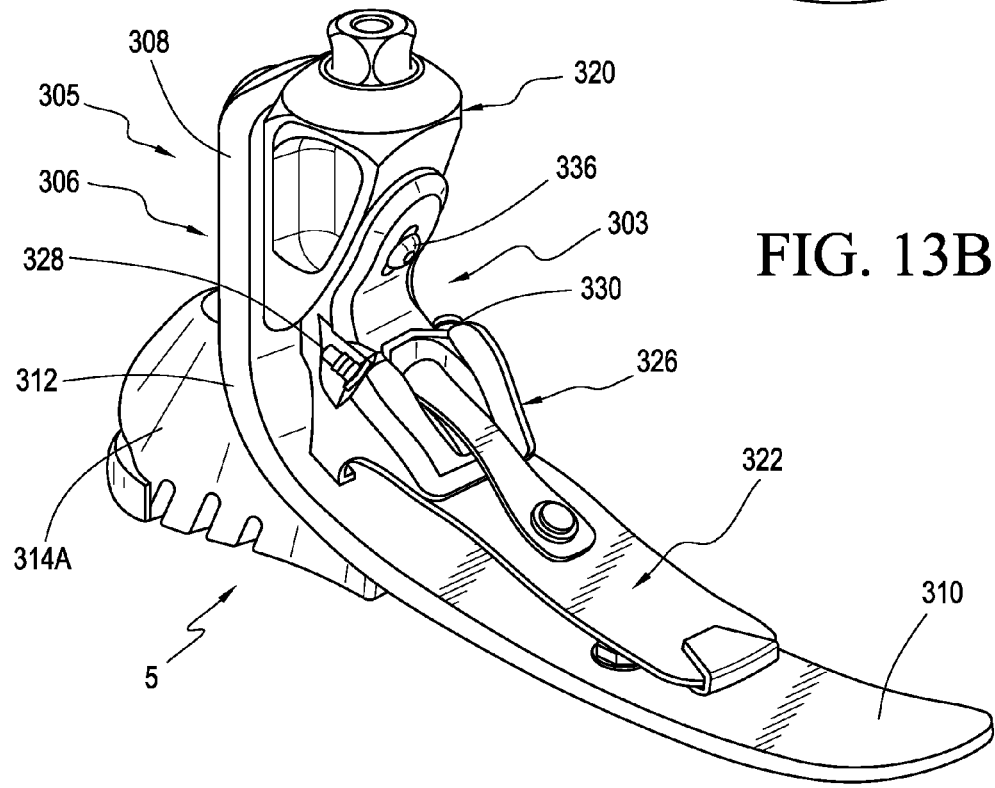
FIG. 13B shows a prosthetic device with a pump mechanism according to another embodiment.
Figure 14:
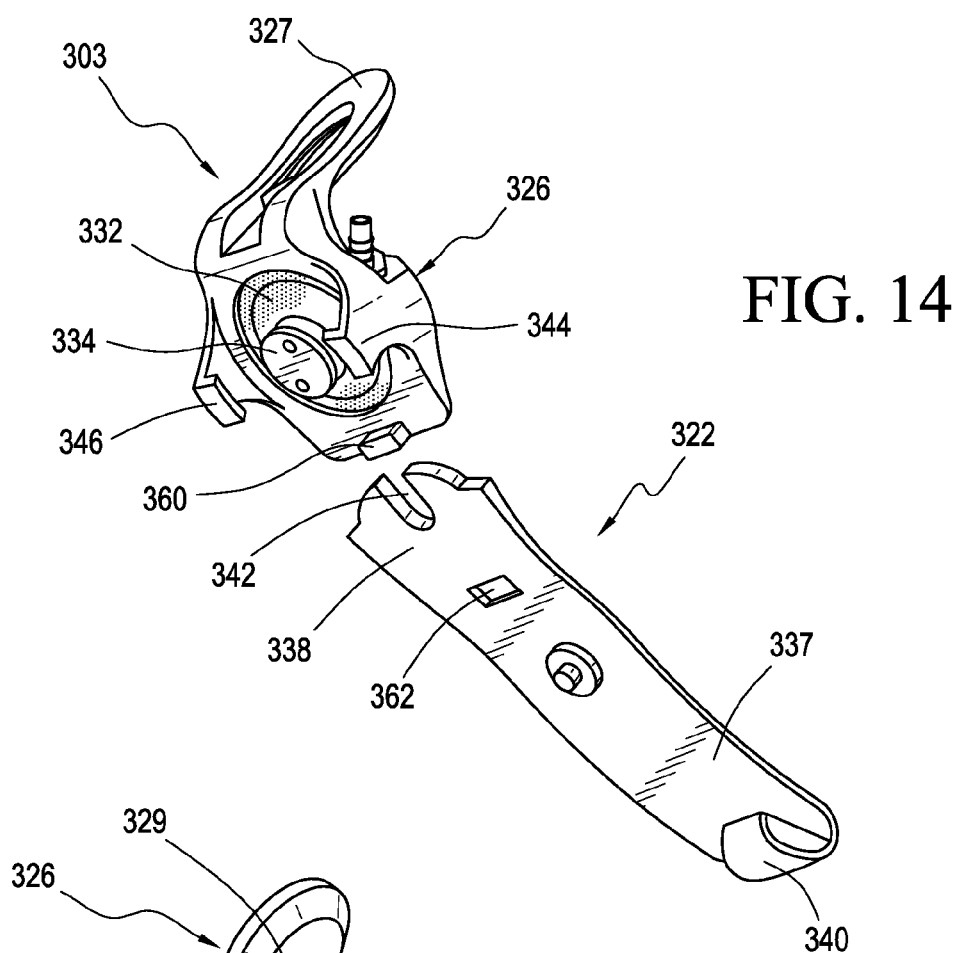
FIG. 14 shows a bottom perspective view of the movable member and pump mechanism shown in FIGS. 13A and 13B.
Figure 15:
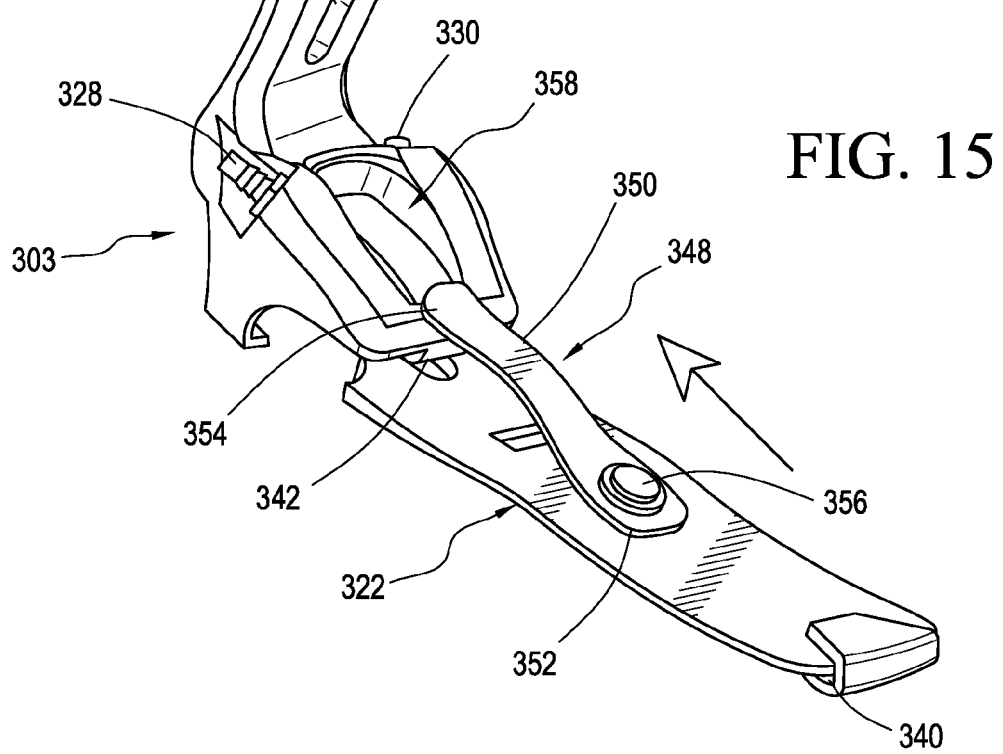
FIG. 15 shows an upper perspective view of the movable member and pump mechanism shown in FIGS. 13A and 13B.

A third embodiment of a prosthetic device 5 is shown in FIGS. 13-15. This embodiment can be similar to the second embodiment described in reference to FIGS. 10-12. The prosthetic foot 305 has a foot member 306 that extends from a first end portion 308 terminating at a first end to a second end portion 310 terminating at a second end. The first end portion 308 can be generally vertically oriented, and the second end portion 310 can be generally horizontally oriented. An intermediate portion 312 of the foot member 306 defining a curvature can have a predetermined length to provide the foot with a desired flexibility.

The prosthetic foot 305 can have a heel member 314. As seen in FIG. 13A, the heel member 314 can extend rearwardly from an anterior end 316 to a free posterior end 318 and is disposed below at least a portion of the foot member 306. The heel member 314 can have a curvilinear profile along its length. A removable wedge insert 324 can be insertable between the heel member 314 and a plantar aspect of the foot member 306 to alter the stiffness of the heel member 314. The removable wedge insert 324 can provide additional shock absorption in the heel member 314.

According to a variation, the heel member can be a resilient heel member 314A as seen in FIG. 13B. The heel member 314A can be made of many materials, including resilient or elastomeric materials such as one or more of foam (e.g., reticulated foam, expanded polyurethane foam), rubber, plastic, polyurethane, and/or other suitable materials. The heel member 314A can be substantially wedge-shaped in a side elevational aspect, increasing in thickness from an anterior portion to a posterior portion.

An adaptor 320 can be coupled to the foot member 306. For instance, the adaptor 320 can be attached to a dorsal aspect of the first end portion 308 of the prosthetic foot 305. Similar to other embodiments, the prosthetic foot 305 can expand and compress.

The pump mechanism 303 is located between the adaptor 320 and a movable member 322 engaging the foot member 306. Movement of the movable member 322 can move the pump mechanism 303 between original and expanded configurations described below.

As seen in FIGS. 14 and 15, the pump mechanism 303 includes a housing 326 containing two one-way valve assemblies 328, 330, a membrane 332, and a connector 334. The valve assembly 328 only allows fluid to enter the pump mechanism 303 which can be in fluid communication with the cavity of a socket. The valve assembly 330 only allows fluid to be expelled out of the pump mechanism 303, preferably to atmosphere. The connector 334 includes an upper radial flange embedded in the membrane 332, a lower radial flange below the membrane 332, and a shaft portion extending between the upper and lower flanges.

Similar to the pump mechanism 2, the pump mechanism 303 relies upon deformation of the membrane 332 to move between an original configuration in which the volume of a fluid chamber defined between the top surface of the membrane 332 and the bottom of the housing 326 is zero or near-zero, and an expanded configuration in which the volume of the fluid chamber is increased. The housing 326 is arranged to surround the outer radial edge portion of the membrane 332 and creates a seal with the membrane 332.

The bottom surface of the housing 326 defines a pair of openings which extend into the housing 326 to form internal passageways to provide fluid communication between the fluid chamber and the two one-way valve assemblies 328, 330.

The housing 326 can be coupled to the adaptor 320 via at least one fastener 336 (shown in FIG. 13A). A posterior surface 327 of the housing 326 can generally complement the anterior surface of the adaptor 320 and can be attached thereto. The posterior surface 327 can have an elongate configuration extending along the anterior surface of the adaptor 320, increasing the attachment surface area between the housing 326 and the adaptor 320, which, in turn, improves attachment strength.

The housing 326 can define a hole 329 (shown in FIG. 15) having an elongate configuration for receiving the fastener 336. This allows the fastener 336 to slide up and down within the hole 329 such that the position of the housing 326 relative to the anterior surface of the adaptor 320 can be varied before a user tightens the fastener to securely attach the housing 326 to the adaptor 320. The positional adjustability of the housing 326 on the adaptor 320 can in turn vary the sensitivity of the pump mechanism 303, which may depend on user activity level, weight, and/or other factors. For instance, by adjusting the position of the housing 326 on the adaptor 320, the level of pre-compression applied to the movable member 322 may be adjusted, varying the sensitivity of the pump mechanism 303 to action of the prosthetic foot 305, advantageously making the pump mechanism 303 customizable to the needs of the user.

The attachment of the pump mechanism 303 to the anterior surface of the adaptor 320 further provides a sleek and low-profile design. It also generally does not substantially affect the functionality of the prosthetic foot 305. In addition, it should be appreciated that the pump mechanism 303 can be a separate add-on module to the prosthetic foot 305. Further, the pump mechanism can be adapted to fit a number of different prosthetic feet, providing versatility.

The movable member 322 is an elongated plate having an anterior end portion 337 and a first portion or posterior end portion 338 and a second portion or anterior end portion 337. The anterior end portion 337 can include a bumper member 340 arranged to engage the dorsal aspect of the prosthetic foot 305 and the posterior end portion 338 is coupled to the membrane 332 via the connector 334. The movable member 322 can have a flexible, rigid, and/or semi-rigid configuration.

A slot or notch 342 is formed in the terminal edge of the posterior end portion 338. The connector 334 can be slidably received within the notch 342 such that a portion of the movable member 322 is located between the bottom surface of the membrane 332 and the lower flange of the connector 334, securing the movable member 322 to the membrane 332.

According to a variation, the housing 326 can define two arms 344, one on each side of the movable member 322 that extend to a location below the movable member 322. Each arm 344 can include a section 346 extending inwardly a distance under the movable member 322, advantageously helping to limit how far the posterior end portion 338 of the movable member 322 can move away from the pump mechanism 303 in response to action of the prosthetic foot 305. The arms 344 also help prevent movement of the movable member 322 from side-to-side.

As seen in FIG. 15, the movable member 322 is removably attached to the housing 326 via a clip mechanism 348. The clip mechanism 348 includes a main body 350 having an anterior end section 352, a posterior end section 354, and a curvilinear profile along its length. The anterior end section 352 can be attached to the movable member 322 via a fastener 356 and the posterior end section 354 is arranged to engage the upper surface of the housing 326 when the movable member 322 is clipped to the housing 326.

The posterior end section 354 is formed so as to bias the clip mechanism 348 toward the upper surface of the movable member 322, whereby the housing 326 can be secured between the lower surface of the posterior end section 354 and the upper surface of the movable member 322.

Through the structure of the clip mechanism 348 and the movable member 322, the movable member 322 has the benefit of being easily and quickly removed from the pump mechanism 303 without the use of tools. The clip mechanism 348 can be made of a durable but flexible material such as carbon fiber cloth, unidirectional composites, plastic, or metal. The length, curvature, and/or shape of the clip mechanism 348 can be adjusted based on the flexibility of the movable member 322 during gait, the length of the movable member 322, and/or other factors.

The upper surface of the housing 326 defines a seat 358 arranged to accommodate the posterior end section 354 of the clip mechanism 348 when the movable member 322 is clipped to the housing 326. This beneficially limits or prevents the clip mechanism 348 from sliding sideways off of the housing 326.

A raised piece 360 (shown in FIG. 14) can be formed on the lower surface of the housing 326. When the movable member 322 is clipped to the housing 326, the raised piece 360 can extend into a corresponding opening 362 defined in the movable member 322, helping to position and secure the movable member 322 on the housing 326.

Upon movement of the prosthetic foot 305 from mid-stance to toe-off, the prosthetic foot 305 moves into compression. In compression, the first and second end portions of the foot member 306 move toward one another causing an anterior edge of the housing 326 to apply a downward force on the upper surface of the movable member 322 and the dorsal aspect of the foot member 306 to apply an upward force on the bumper member 340 of the movable member 322.

The upward force on the bumper member 340 causes the movable member 322 to pivot and/or flex around the anterior edge of the housing 326, which, in turn, moves the posterior end section 354 of the movable member 322 away from the housing 326. As the posterior end section 354 moves downwardly away from the housing 326, the clip mechanism 348 flexes as it is forced away from the movable member 322.

The movement of the posterior end section 354 away from the housing 326 moves the pump mechanism 303 to the expanded configuration, increasing the volume of the fluid chamber to create a vacuum in the pump mechanism 303 and to pull fluid into the pump mechanism 303 through the one-way valve assembly 328.

At the end of the stance phase or when the weight of the user is removed from the prosthetic foot 305, the prosthetic foot 305 returns to its resting position and the properties of the material of the clip mechanism 348 can help return the posterior end portion 354 of the movable member 322 toward the housing 326, moving the pump mechanism 303 back toward its original configuration and decreasing the volume of the fluid chamber to a zero or near zero volume. During the return of the pump mechanism 303 toward its original configuration, the pump mechanism 303 expels fluid in the fluid chamber out the one-way valve assembly 330.

Fourth Embodiment of the Prosthetic Device

Figure 16:
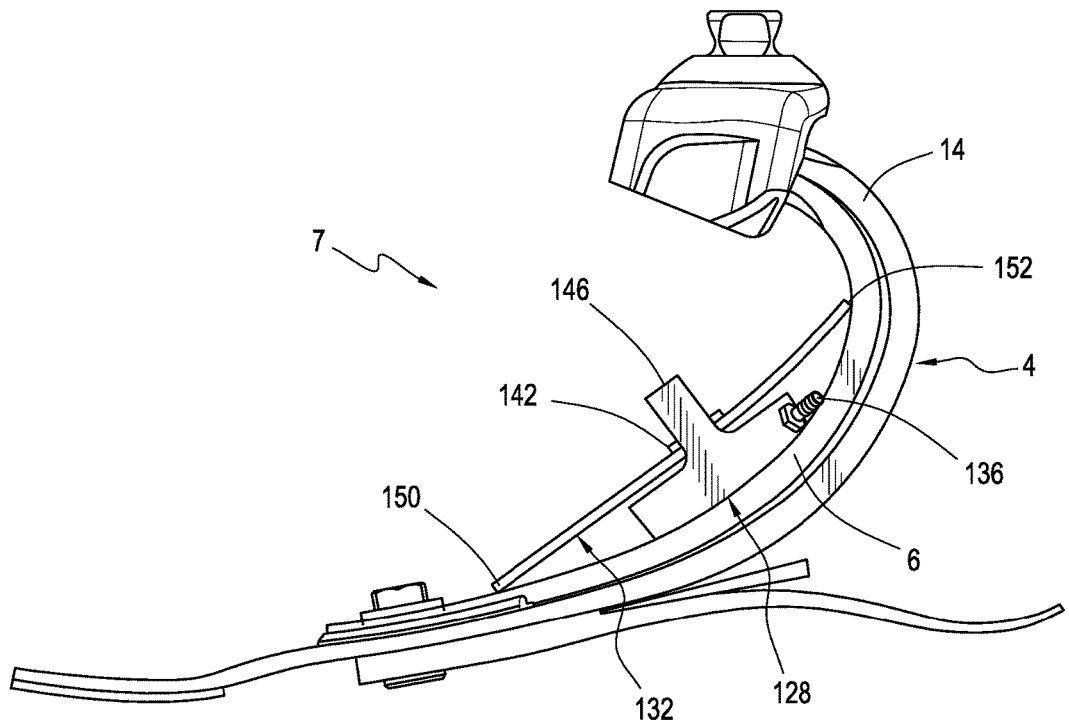
FIG. 16 shows a side view of a prosthetic device with a pump mechanism according to another embodiment.
Figure 17:
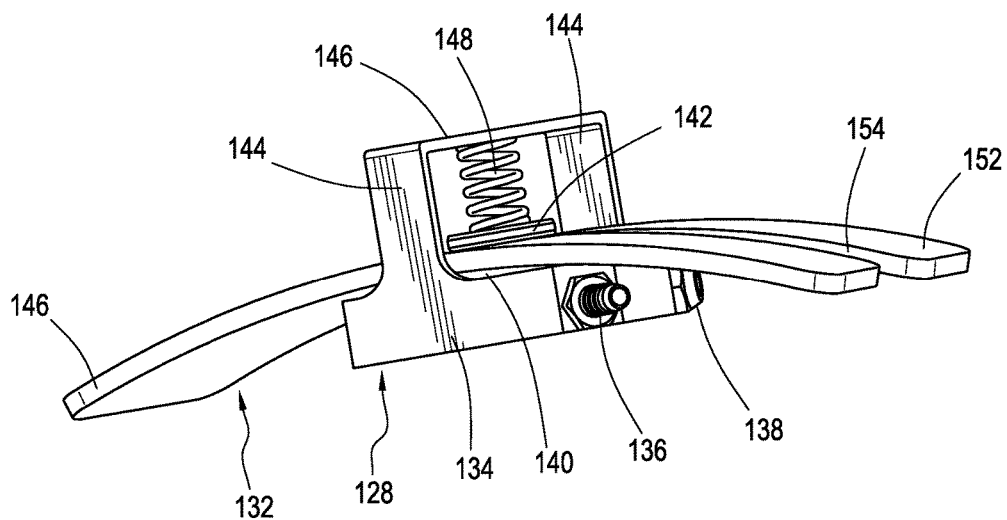
FIG. 17 shows the pump mechanism of FIG. 16 removed from the prosthetic device for ease of reference.

A fourth embodiment of a prosthetic device 7 is shown in FIGS. 16 and 17. The prosthetic device 7 includes a prosthetic foot 4 and a pump mechanism 128 arranged on the dorsal aspect of the prosthetic foot 4 or upper foot member 6. The pump mechanism 128 can be secured to the prosthetic foot 4 in any suitable manner. The pump mechanism 128 is operable between the upper foot member 6 of the prosthetic foot 4 and a movable member 132 operably coupled to the pump mechanism 128 and arranged to slidably engage the dorsal aspect of the prosthetic foot 4.

The pump mechanism 128 includes a housing 134 containing two valve assemblies 136, 138, a membrane 140, and a connector 142. The valve assembly 136 only allows fluid to enter the pump mechanism 128 which can be in fluid communication with the cavity of a socket. The valve assembly 138 only allows fluid to be expelled out of the pump mechanism 128, preferably to atmosphere. The connector 142 includes a lower flange embedded in the membrane 140, an upper flange above the membrane 140, and a shaft portion extending between the upper and lower flange.

The housing 134 defines two arms 144 on each side of the movable member 132 that extend to a location above the movable member 132. A cross member 146 is connected between the arms 144 above the movable member 132. A biasing mechanism 148 is arranged to bias the movable member 132 toward the main body portion of the housing 134. The biasing mechanism 148 can be a coiled spring or other suitable member located between the cross member 146 and the upper surface of the movable member 132. While one biasing mechanism is shown, it will be appreciated that the pump mechanism 128 can include two, three, or any other suitable number of biasing mechanisms.

Similar to the previously described pump mechanisms, the pump mechanism 128 relies upon deformation of the membrane 140 to move between an original configuration in which the volume of a fluid chamber defined between the lower surface of the membrane 140 and the bottom of the housing 134 is zero or near-zero, and an expanded configuration in which the volume of the fluid chamber is increased. The housing 134 is arranged to surround the outer radial edge portion of the membrane 140 and creates a seal with the membrane 140. The upper surface of the housing 134 defines a pair of openings which extend into the housing 134 to form internal passageways to provide fluid communication between the fluid chamber and the two one-way valve assemblies 136, 138.

The movable member 132 can be an arcuate or substantially straight member having a first portion or posterior end portion 152 and a second portion or an anterior end portion 150. Both the anterior and posterior end portions 150, 152 are arranged to slidably engage the dorsal aspect of the prosthetic foot 4. The movable member 132 is coupled to the membrane 140 via the connector 142. For instance, a slot 154 can be formed in the terminal edge of the posterior end portion 152. The connector 142 can be slidably received within the slot 154 such that a portion of the movable member 132 is located between the upper surface of the membrane 140 and the upper flange of the connector 142, securing the movable member 132 to the membrane 140. The connector 142 and the membrane 140 can be connected to the movable member 132 at or near a center of the movable member 132. In some embodiments, the movable member 132 can be rigid or semi-rigid.

Movement of the foot members 6, 14 between expansion and compression moves the movable member 132 to operate the pump mechanism 128. For instance, upon mid-stance and/or toe-off, the prosthetic foot 4 moves into compression as the first and second end portions of the foot members 6, 14 move toward one another. This causes upper foot member 6 to apply a radially outward or upward force on the posterior end portion 152 of the movable member 132.

This force exerted on the posterior end portion 152 causes the movable member 132 to pivot about the anterior end portion 150 of the movable member 132 on the upper foot member 6, which, in turn, rotates the posterior end portion 152 of the movable member 132 away from the main body of the housing 134 and toward the cross member 146. As the movable member 132 moves toward the cross member 146, the biasing mechanism 148 is compressed between the cross member 146 and the movable member 132. The connector 142 is able to slide along a length of the slot 154 in the movable member 132 to accommodate movement of the movable member 132.

The movement of the movable member 132 away from the housing 134 also moves the pump mechanism 128 to the expanded configuration, increasing the volume of the fluid chamber to generate a vacuum in the pump mechanism 128 for pulling fluid into the pump mechanism 128 through the valve assembly 136.

At the end of the stance phase or when the weight of the user is removed from the prosthetic foot 4, the prosthetic foot 4 returns to its resting position and the energy stored in the biasing mechanism 148 drives the posterior end portion 152 of the movable member 132 back toward the housing 134, moving the pump mechanism 128 back toward its original configuration and decreasing the volume of the fluid chamber to a zero or near zero volume. During the return of the pump mechanism 128 toward its original configuration, the pump mechanism 128 expels fluid in the fluid chamber out the one-way valve assembly 138. Because the pump mechanism 128 returns to its original configuration of zero or near-zero volume in the fluid chamber at the beginning or end of each gait cycle, all fluid drawn into the pump mechanism 128 can be automatically expelled.

Fifth Embodiment of the Prosthetic Device

Figure 18:
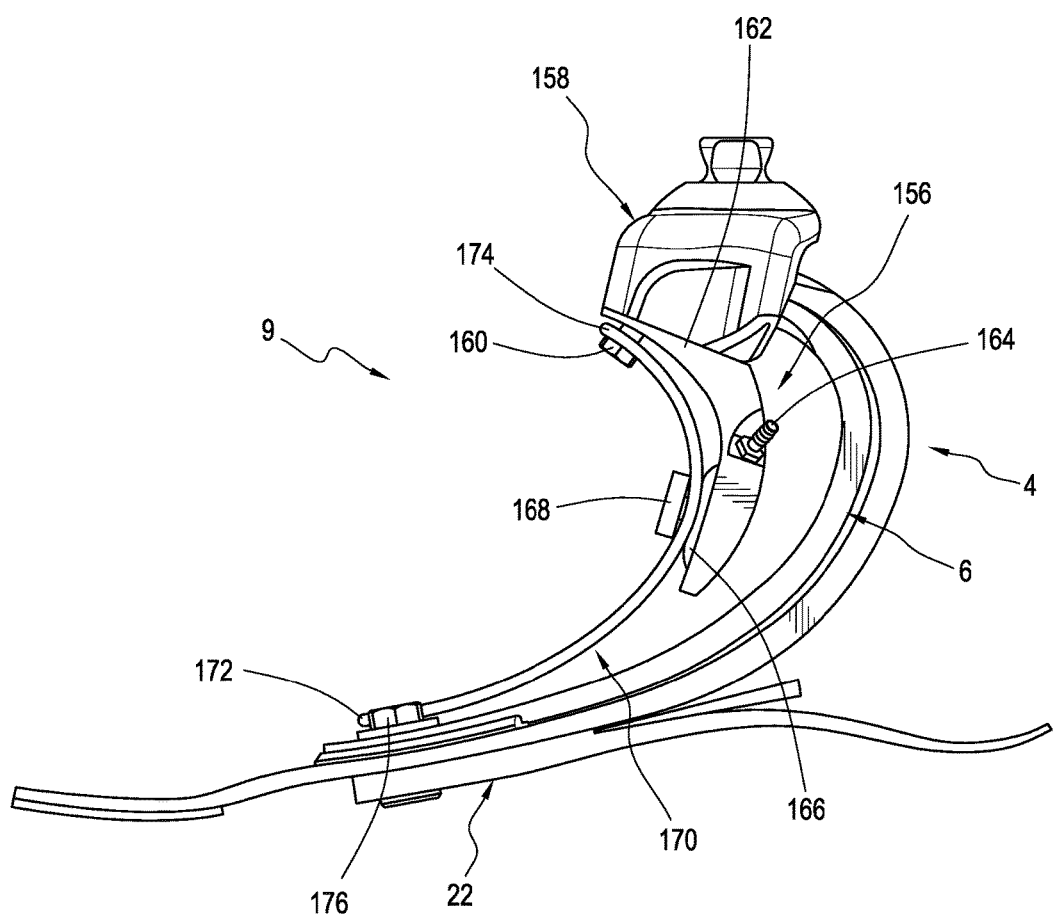
FIG. 18 shows a side view of a prosthetic device with a pump mechanism according to another embodiment.

A fifth embodiment of a prosthetic device 9 is shown in FIG. 18. This embodiment can be similar to the previously described embodiments except that the pump mechanism moves to the expanded configuration at heel strike rather mid-stance and/or toe off.

The prosthetic device 9 includes a prosthetic foot 4 and a pump mechanism 156. The pump mechanism 156 is coupled to the lower surface of the adaptor 158 via a fastener 160 or any other suitable means. The pump mechanism 156 includes a housing 162 containing one-way valve assemblies 164, a membrane 166, and a connector 168. One of the valve assemblies 164 is arranged to only allow fluid to enter the pump mechanism 156. The other valve assembly 164 is arranged to only allow fluid to be expelled out of the pump mechanism 156. The connector 168 includes an upper radial flange external to the membrane 166, a lower radial flange embedded in the membrane 166, and a shaft portion extending between the upper and lower flange.

An upper surface of the housing 162 can generally complement the lower surface of the adaptor 158. An anterior surface of the housing 162 is curved between the upper surface of the housing 162 and a lower surface. A posterior surface of the housing 162 is curved between the upper and lower surfaces of the housing 162.

The anterior surface of the housing 162 defines a cavity that is provided with an undercut circumferential groove between an open end of the cavity and a closed bottom of the cavity. An outer radial edge portion of the membrane 166 can be situated in the circumferential groove such that a seal is formed between the membrane 166 and the housing 162. The bottom of the cavity can include openings which extend into the housing 162 to form internal passageways providing fluid communication between a fluid chamber defined below and the one-way valve assemblies 164.

The pump mechanism 156 is movable between an original configuration in which the volume of a fluid chamber defined between the bottom surface of the membrane 166 and the bottom of the cavity is zero or near-zero, and an expanded configuration in which the volume of the fluid chamber is increased. The bottom of the cavity can substantially complement the bottom surface of the membrane such that when no force is exerted on the pump mechanism 156 it is in the original configuration.

Similar to the other embodiments, the pump mechanism 156 relies upon deformation of the membrane 166 to move between the original configuration and the expanded configuration.

The movable member 170 is an arcuate or curved plate including a first portion or a posterior end portion 174 and second portion or anterior end portion 172. The anterior end portion 172 can be attached to the prosthetic foot 4 at or near the anterior end of the upper foot member 6 via a fastener 176 or other suitable means. In some embodiments, the fastener 176 can be the same fastener attaching the heel member to the prosthetic foot 4. The posterior end portion 174 can be attached to the housing 162 via the fastener 160. The movable member 170 is connected to the prosthetic foot 4 such that the pump mechanism 156 is located between the movable member 170 and the dorsal aspect of the upper foot member 6. As seen, the curvature of the movable member 170 can generally complement the curvature of the anterior surface of the housing 162.

The movable member 170 is coupled to the membrane 166 via the connector 168. The movable member 170 defines a slot in a terminal edge of the posterior end portion 174 that extends along a portion of the length of the movable member 170. The shaft portion of the connector 168 is slidably received within the slot such that the movable member 170 is located between the upper surface of the membrane 166 and the upper flange of the connector 168. In other embodiments, the movable member 170 can define a through hole arranged to receive the shaft portion of the connector 168.

Compression and expansion of the foot members 6, 14 flexes or moves the movable member 170 to operate the pump mechanism 156. For instance, the prosthetic foot 4 is in its resting position in FIG. 18. When the prosthetic foot 4 is in its resting position, the pump mechanism 156 is in its original configuration. Upon heel strike, the prosthetic foot 4 moves to the expanded position, which, in turn, increases the radius of curvature of the movable member 170 as the first and second end portions of the upper and lower foot members 6, 14 move apart.

This increase of the radius of curvature or straightening out of the movable member 170 pulls the membrane 166 away from the housing 162 to deform the membrane 166 between the movable member 170 and the housing 162, increasing the volume of the fluid chamber. This creates a vacuum in the pump mechanism 156, pulling fluid into the pump mechanism 156 through one of the one-way valve assemblies 164. It should be appreciated that the connector can slide within the slot of the movable member 170 as the movable member 170 bends and flexes.

As the prosthetic foot 4 moves from heel strike through mid-stance and/or toe-off, the prosthetic foot 4 moves into compression. In compression, the first and second end portions of the foot members 6, 14 move toward one another causing the radius curvature of the movable member 170 to decrease, which, in turn, forces the pump mechanism 156 back toward its original configuration and decreases the volume of the fluid chamber to a zero or near zero volume. During the return of the membrane 166 toward the housing 162, the pump mechanism 156 expels fluid in the fluid chamber out of one of the one-way valve assemblies 164. Because the pump mechanism 156 returns to its original configuration of zero or near-zero volume in the fluid chamber at mid-stance and/or toe-off, all fluid drawn into the pump mechanism 156 can be automatically expelled rather than relying on complete compression cycle of the pump to expel air drawn in from the socket as in the prior art.

At the end of the stance phase, the prosthetic foot 4 returns to its resting position and the properties of the movable member 170 can help maintain the pump mechanism 156 in its original configuration.

Sixth Embodiment of the Prosthetic Device

Figure 19:
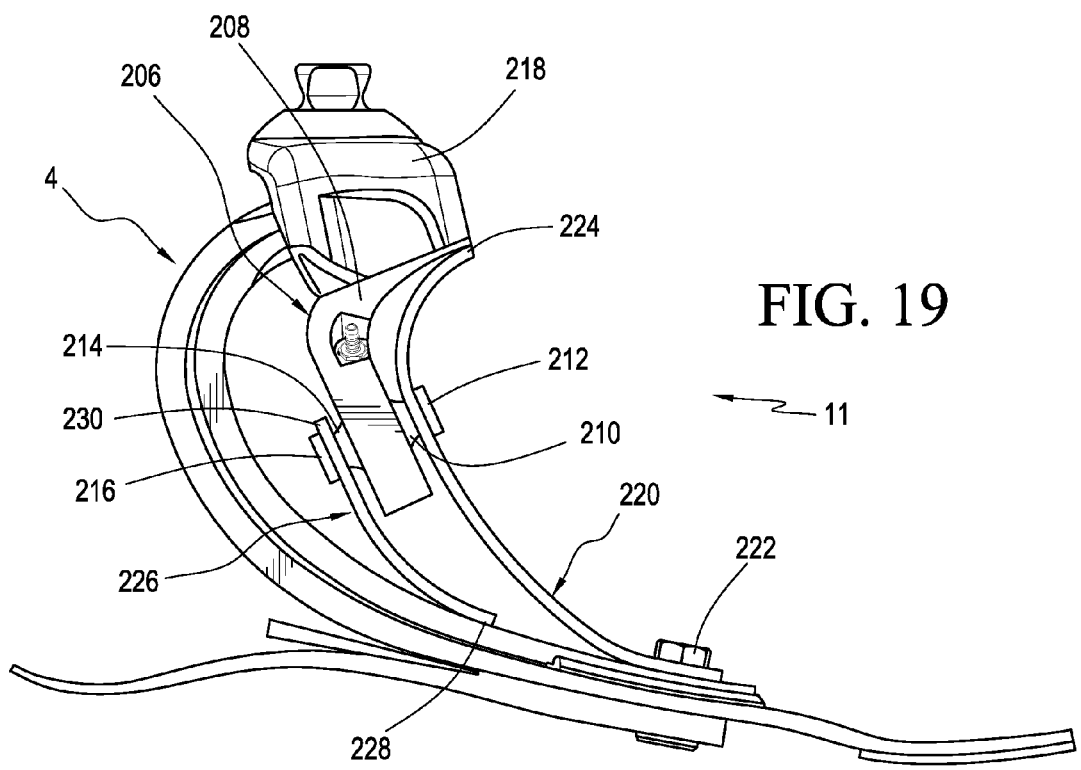
FIG. 19 shows a side view of a prosthetic device with a pump mechanism according to another embodiment.
Figure 20:
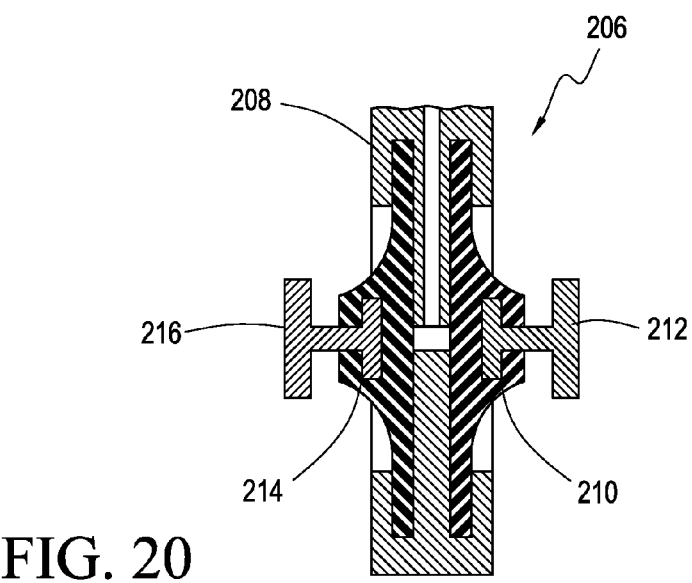
FIG. 20 shows a cross-section of the pump mechanism in FIG. 19.

A sixth embodiment of a prosthetic device 11 is shown in FIGS. 19 and 20. This embodiment includes a dual-membrane pump mechanism that can create a vacuum at mid-stance, heel strike, and toe-off. For instance, the prosthetic device 11 includes a prosthetic foot 4 and a pump mechanism 206. The pump mechanism 206 includes a housing 208, at least one one-way outlet valve assembly and at least one one-way inlet valve assembly, a first membrane 210, a first connector 212, a second membrane 214, and a second connector 216. The first connector 212 includes an upper radial flange above the first membrane 210, a lower radial flange embedded in the first membrane 210, and a shaft portion extending between the upper and lower radial flanges. The second connector 216 includes an upper radial flange embedded in the second membrane 214, a lower radial flange below the second membrane 214, and a shaft portion extending between the upper and lower flanges.

The upper surface of the housing 208 generally complements the lower surface of the adaptor 218 on the prosthetic foot 4. An anterior surface of the housing 208 is curved between the upper surface and a lower surface of the housing 208. A posterior surface of the housing 208 is curved between the upper and lower surfaces of the housing 208. The anterior surface of the housing 208 defines a first cavity that is provided with an undercut circumferential groove between an open end of the first cavity and a closed bottom of the first cavity. An outer radial edge of the first membrane 210 can be situated in the circumferential groove such that a seal is formed between the first membrane 210 and the housing 208.

The posterior surface of the housing 208 defines a second cavity that is provided with an undercut circumferential groove between an open end of the second cavity and a closed bottom of the second cavity. An outer radial edge of the second membrane 214 can be situated in the circumferential groove such that a seal is formed between the second membrane 214 and the housing 208. The bottom of the cavities can include openings which extend into the housing 208 to form internal passageways providing fluid communication between the fluid chambers defined below and/or the one-way valve assemblies.

The first membrane 210 of the pump mechanism 206 is movable between an original configuration in which the volume of a first fluid chamber defined between the bottom surface of the first membrane 210 and the bottom of the first cavity is zero or near-zero, and an expanded configuration in which the volume of the first fluid chamber is increased.

The second membrane 214 of the pump mechanism is movable between an original configuration in which the volume of a second fluid chamber defined between the upper surface of the second membrane 214 and the bottom of the second cavity is zero or near-zero, and an expanded configuration in which the volume of the second fluid chamber is increased.

Similar to the other embodiments, the pump mechanism 206 relies upon deformation of the membranes to move between the original and expanded configurations.

A first movable member 220 is an arcuate plate including a first portion or a posterior end portion 224 and a second portion or an anterior end portion 222. The anterior end portion 222 is attached to the prosthetic foot 4 at or near the second or anterior end of the upper foot member 6. The posterior end portion 224 can be attached to the housing 208. The first movable member 220 is connected to the prosthetic foot 4 such that the pump mechanism 206 is located between the first movable member 220 and the upper surface of the upper foot member 6. The first movable member 220 is coupled to the first membrane 210 via the first connector 212.

A second movable member 226 is an elongated plate extending at an angle between the upper foot member 6 and the second membrane 214. The second movable member 226 includes a second portion or an anterior end portion 228 arranged to engage the dorsal aspect of the prosthetic foot 4 and a first portion or posterior end portion 230 is coupled to the second membrane 214 via the second connector 216. The second movable member 226 is arranged to engage a posterior edge of the housing 208.

When the prosthetic foot 4 is in the resting position, the first and second membranes 210, 214 are in the original configuration. Upon heel strike, the prosthetic foot 4 moves into expansion, which, in turn, moves the first membrane 210 to its expanded configuration and leaves the second membrane 214 in its original configuration. In expansion, the prosthetic foot 4 increases the radius of curvature of the first movable member 220 as the first and second end portions of the upper foot member 6 move apart.

This increase of the radius of curvature or straightening out of the first movable member 220 pulls the first membrane 210 away from the housing 208 to deform the first membrane 210 between the first movable member 220 and the housing 208, increasing the volume of the first fluid chamber. This has the effect of creating a vacuum in the first fluid chamber of the pump mechanism 206, pulling fluid into the first fluid chamber through the one-way inlet valve assembly.

In expansion, the prosthetic foot 4 also lifts or slides the anterior end portion 228 of the second movable member 226 along a length of the prosthetic foot 4 without necessarily flexing or bending the second movable member 226, thus leaving the second membrane 214 in the original configuration.

As the prosthetic foot 4 moves from heel strike back toward its resting position, the properties of the first movable member 220 and the action of the foot can help return the first movable member 220 to its un-flexed state, moving the first membrane 210 back toward its original configuration and decreasing the volume of the first fluid chamber to a zero or near-zero volume. During the return of the first membrane 210 toward the housing 208, the pump mechanism 206 can expel fluid from the fluid chambers out of a one-way valve assembly.

As the prosthetic foot 4 moves from its resting position through mid-stance and/or toe-off, the prosthetic foot 4 moves into compression, which, in turn, moves the second membrane 214 to its expanded configuration. With the prosthetic foot 4 in compression, the posterior edge of the housing 208 applies a downward force on the upper surface of the second movable member 226 and the intermediate portion 12 of the upper foot member 6 applies an upward force on the lower surface of the anterior end portion 228 of the second movable member 226.

The upward force on the lower surface of the anterior end portion 228 causes the second movable member 226 to pivot and/or flex around the posterior edge of the housing 208, which, in turn, moves the posterior end portion 230 of the second movable member 226 away from the housing 208.

As the posterior end portion 230 moves away from the housing 208, it pulls the second membrane 214 away from the housing 208, moving the second membrane 214 to the expanded configuration and increasing the volume of the second fluid chamber. This has the effect of generating a vacuum in the second fluid chamber, pulling fluid into the pump mechanism 206 through the one-way inlet valve assembly.

In compression, the first and second end portions of the foot members 6, 14 move toward one another causing the radius of curvature of the first movable member 220 to decrease, which, in turn, maintains the first membrane 210 its original configuration. Compression of the prosthetic foot 4 thus also automatically creates a vacuum in the pump mechanism, pulling fluid into the pump mechanism from the socket and thereby increasing the efficiency of the pump mechanism by pulling a vacuum in both compression and expansion of the prosthetic foot 4.

At the end of the stance phase or when the weight of the user is removed from the prosthetic foot 4, the prosthetic foot returns to its resting position and the properties of the second movable member 226 can help return the second movable member 226 to its un-flexed state, moving the second membrane 214 back toward its original configuration and decreasing the volume of the second fluid chamber to a zero or near zero volume. During the return of the second membrane 214 toward the housing 208, the pump mechanism 206 expels fluid from the second fluid chamber out of the one-way outlet valve assembly.

Thus the pump mechanism 206 advantageously can be activated during heel-strike, mid stance, and toe-off. More particularly, depending on whether the prosthetic foot is in compression or expansion, the movable members will pull one or the other membrane on the pump mechanism 206, creating a vacuum.

Seventh Embodiment of the Prosthetic Device

Figure 21:
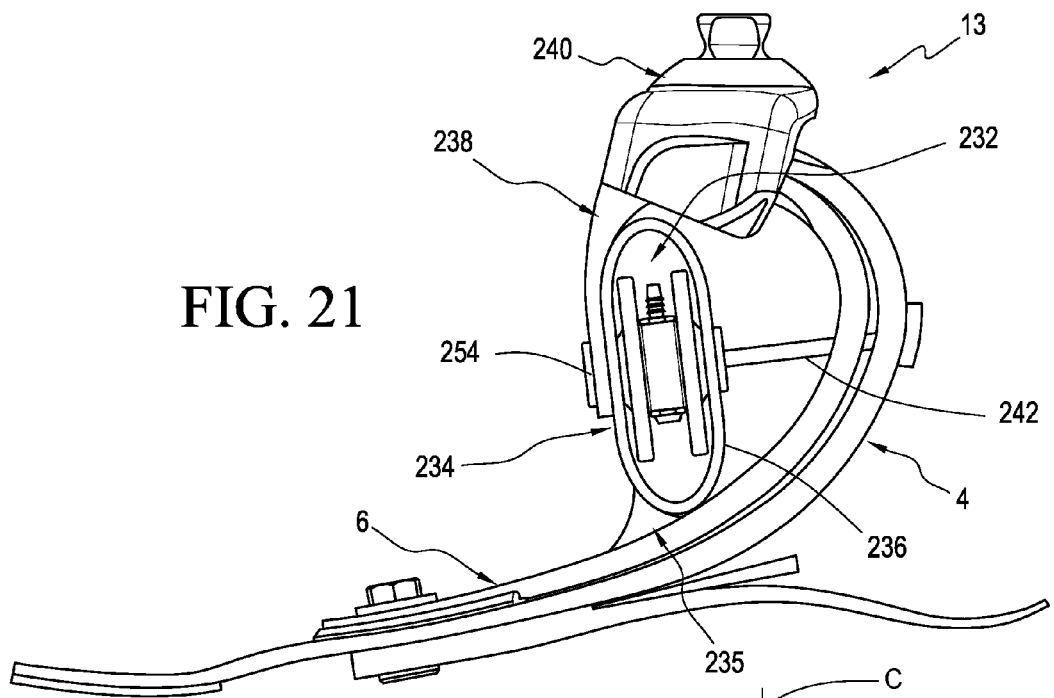
FIG. 21 shows a prosthetic device with a pump mechanism according to another embodiment.
Figure 22:
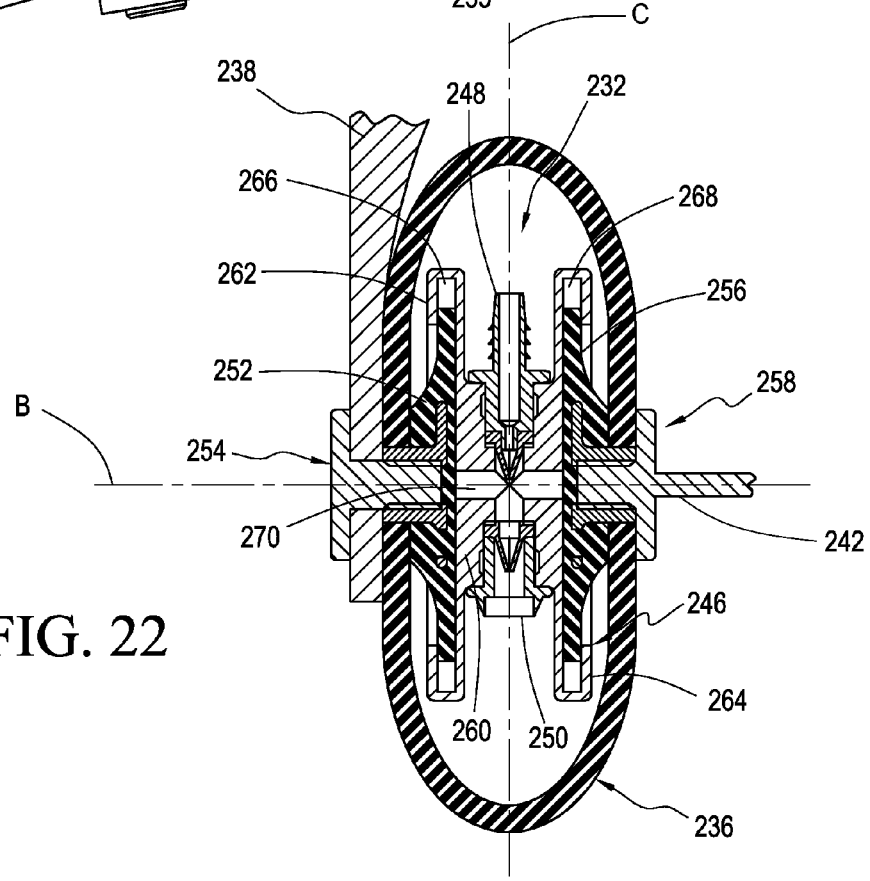
FIG. 22 shows a cross section of the pump mechanism in FIG. 21.

A seventh embodiment of a prosthetic device 13 is shown in FIGS. 21 and 22. This embodiment includes a flexible enclosure in combination with a dual-membrane pump mechanism which can create a vacuum at mid-stance, heel strike, and toe-off. For instance, the prosthetic device 13 includes a prosthetic foot 4 and a pump mechanism 232. The pump mechanism 232 can comprise a dual membrane pump mechanism similar to any of the dual membrane pump mechanisms previously described. The pump mechanism 232 can include a first membrane and first connector 254 on the anterior side of the pump mechanism 232 and a second membrane and a second connector 258 on the posterior side of the pump mechanism 232.

A support member 238 having an elongate configuration extends downwardly from the adaptor 240 on the prosthetic foot 4. The support member 238 can include an upper surface that generally complements the lower surface of the adaptor 240. An anterior surface of the support member 238 is convexly curved between the upper surface and a lower surface of the support member 238. A posterior surface of the support member 238 is concavely curved between the upper and lower surface. The posterior surface of the support member 238 can generally complement the curvature of the movable member described below.

A stop 235 having a wedge-like configuration is secured to the intermediate portion 12 of the upper foot member 6 at a location generally below the support member 238. The stop 235 can include a bottom surface that generally complements the upper surface of the intermediate portion 12. A posterior surface of the stop 235 is concavely curved and generally complements the curvature of the movable member.

The pump mechanism 232 can be situated within a movable member 234 comprising a flexible enclosure 236 having an elliptical configuration. The flexible enclosure 236 is coupled to the pump mechanism 232 via the first and second connectors. The flexible enclosure 236 includes a first portion arranged to slidably engage the dorsal aspect of the prosthetic foot 4 and a second portion coupled to the pump mechanism 232. The flexible enclosure 236 can be made of a durable but flexible material such as carbon fiber cloth, unidirectional composites, plastic, and/or metal. The configuration of the flexible enclosure 236 can be adjusted based on the flexibility of the prosthetic foot during gait, the length of the prosthetic foot, the weight of the user, and/or other factors.

The flexible enclosure 236 is situated between the intermediate portion 12 of the upper foot member 6 and the adaptor 240 such that a first axis C of the flexible enclosure 236 generally extends between the adaptor 240 and the intermediate portion 12 and a second axis B of the flexible enclosure 236 generally extends from an anterior end of the support member 238 toward the posterior of the prosthetic foot 4. The first axis C can be a major axis and the second axis B can be a minor axis. An anterior wall of the flexible enclosure can be arranged to be positioned at or near the posterior surfaces of the support member 238 and the stop 235.

The posterior wall of the flexible enclosure 236 is attached to the posterior of the prosthetic foot 4. An anchor member 242 extending from the posterior of the prosthetic foot 4 attaches the posterior wall of the flexible enclosure 236 to the prosthetic foot 4. The anterior wall of the flexible enclosure 236 is attached to the posterior surface of the support member 238. The first connector 254 extending through the anterior end area of the support member 238 attaches the anterior wall of the flexible enclosure 236 to the support member 238. The anchor member 242 is connected to the second connector 256.

When the prosthetic foot 4 is in the resting position, both the first and second membranes can be in the original configuration as previously described. Upon heel strike, the prosthetic foot 4 moves into expansion, which in, causes the anchor member 242 and/or the first connector 254 to pull on the flexible enclosure 236 generally along the second axis B of the flexible enclosure 236. As the anchor member 242 and/or the first connector 254 pull on the flexible enclosure 236, the anterior and posterior sides of the flexible enclosure 236 are forced apart, which, in turn, causes the connectors coupled to the flexible enclosure 236 to pull the first and/or second membranes away from the housing of the pump mechanism 232, increasing the volume of fluid chambers defined between the membranes and the housing.

This increase in volume of the fluid chambers creates a vacuum in the fluid chambers, pulling fluid into the fluid chambers through a one-way inlet valve assembly. The pump mechanism 232 advantageously deforms both membranes at substantially the same time upon expansion of the prosthetic foot, creating a better attachment between the residual limb and the socket.

As the prosthetic foot 4 moves from heel strike back toward its resting position, the properties of the flexible enclosure 236 can help return the flexible enclosure 236 to its un-flexed state, moving the membranes back toward their original configuration and decreasing the volume of the fluid chambers to a zero or near-zero volume. During the return of the membranes toward the housing, the pump mechanism 232 can expel fluid from the fluid chambers out of a one-way outlet valve assembly.

As the prosthetic foot moves from its resting position into compression, the top and bottom of the flexible enclosure 236 are compressed between the adaptor 240 and the intermediate portion 12 of the upper foot member 6. This forces the anterior and posterior sides of the flexible enclosure 236 apart, which, in turn, causes the connectors coupled to the flexible enclosure 236 to pull the first and/or second membranes away from the housing of the pump mechanism 232, increasing the volume of fluid chambers defined between the membranes and the housing. Again, this increase in volume of the fluid chambers creates a vacuum in the fluid chambers, pulling fluid into both of the fluid chambers through the one-way inlet valve assembly. It will be appreciated that in some embodiments the fluid chambers can be in fluid communication such that the fluid chambers can be considered a single fluid chamber.

At the end of the stance phase or when the weight of the user is removed from the prosthetic foot, the prosthetic foot 4 returns to its resting position and the properties of the flexible enclosure 236 can help return the flexible enclosure 236 to its un-flexed state, moving the membranes back toward their original configuration and decreasing the volume of the fluid chambers to a zero or near-zero volume. During the return of the membranes toward the housing, the pump mechanism 232 can expel fluids from the fluid chambers out of a one-way outlet valve assembly.

The pump mechanism 232 advantageously can generate a vacuum when it is compressed (top to bottom) or expanded (from side to side). This helps the prosthetic device to draw fluid out of the socket when the prosthetic foot 4 is either in compression or expansion.

The pump mechanism 232 includes a housing 246 containing two one-way valve assemblies 248, 250, the first membrane 252, the first connector 254, the second membrane 256, and the second connector 258. The valve assembly 248 is arranged to only allow fluid to enter the pump mechanism 232. When the volume of the pump mechanism 232 increases, fluid can be drawn out from the socket via the valve assembly 248. The valve assembly 250 is arranged to only allow fluid to be expelled out of the pump mechanism 232, preferably to atmosphere.

The housing 246 includes a main body 260 and an anterior radial flange 262 and a posterior radial flange 264 connected to opposite sides of the main body 260. As seen, the valve assemblies 248, 250 can be located between the anterior and posterior flange 262, 264. This can help protect the valve assemblies 248, 250 from being inadvertently damaged or hit during use.

The outer surface of the anterior flange 262 facing the anterior wall of the flexible enclosure 236 defines a first cavity 266 that is provided with an undercut circumferential groove between an open end of the first cavity 266 and a closed bottom of the cavity 266. An outer radial edge portion of the first membrane 252 can be situated in the circumferential groove such that a seal is formed between the first membrane 252 and the housing 246. The first membrane 252 is movable between an original configuration in which the volume of a first fluid chamber defined between the bottom surface of the first membrane 252 and the bottom of the first cavity 266 is zero or near-zero, and an expanded configuration in which the volume of the first fluid chamber is increased.

The outer surface of the posterior flange 264 facing the posterior wall of the flexible enclosure 236 defines a second cavity 268 that is provided with an undercut circumferential groove between an open end of the second cavity 268 and a closed bottom of the second cavity 268. An outer radial edge of the second membrane 256 can be situated in the circumferential groove such that a seal is formed between the second membrane 256 and the housing 246. The second membrane 256 is movable between an original configuration in which the volume of a second fluid chamber defined between the bottom surface of the second membrane 256 and the bottom of the second cavity 268 is zero or near-zero, and an expanded configuration in which the volume of the second fluid chamber is increased.

Similar to the other embodiments, the pump mechanism 232 relies upon deformation of the membranes 252, 256 to move between the original and expanded configurations.

The bottom of one or more of the cavities 266, 268 has at least one opening which extends into the housing 246 for form internal passageways providing fluid communication between the fluid chambers and the one-way valve assemblies 248, 250. Optionally, the housing 246 can define an internal passageway 270 extending between the first and second fluid chambers and the valve assemblies 248, 250 such that the first and second fluid chambers comprise a single fluid chamber.

The first connector 254 includes a first radial flange external to the first membrane 252, a second radial flange embedded in the first membrane 252, and a shaft portion extending between the first and second flanges. The second connector 258 includes a first radial flange embedded in the second membrane 256, a second radial flange external to the second membrane 256, and a shaft portion extending between the first and second flanges.

The flexible enclosure 236 is generally an elliptical ring member and is coupled to the first membrane 252 via the first connector 254. The flexible enclosure 236 defines a first through hole. The shaft portion of the first connector 254 extends through the first through hole such that the anterior wall of the flexible enclosure 236 is secured between the first flange of the first connector 254 and the first membrane 252.

The flexible enclosure 236 also defines a second through hole. The shaft portion of the second connector 258 extends through the second through hole such that the posterior wall of the flexible enclosure 236 is secured between the second flange of the second connector 258 and the second membrane 256. As such, when the anterior and posterior walls of the flexible enclosure 236 move relative to one another, the flexible enclosure moves the membranes 252, 256 between the original and expanded configurations.

Eighth Embodiment of the Prosthetic Device

Figure 23:
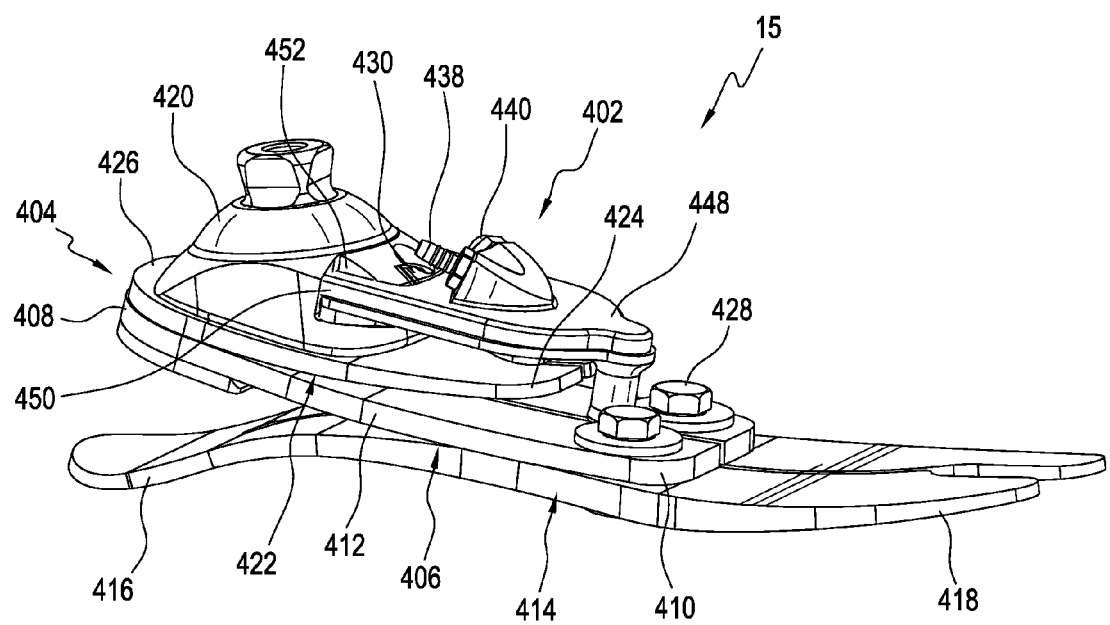
FIG. 23 shows a prosthetic device with a pump mechanism according to another embodiment.
Figure 24:
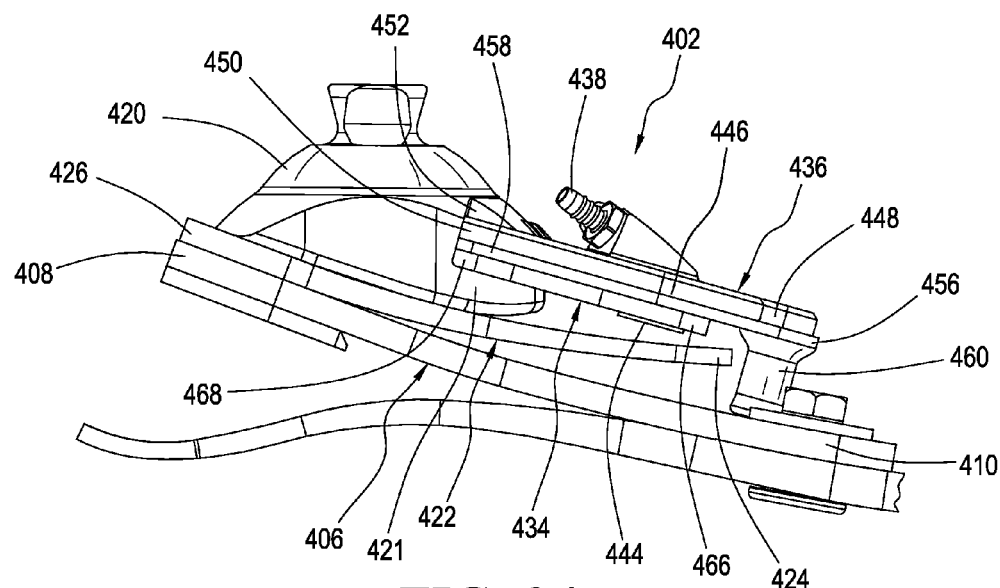
FIG. 24 shows a partial side view of the prosthetic device in FIG. 23 in a first position.
Figure 25:
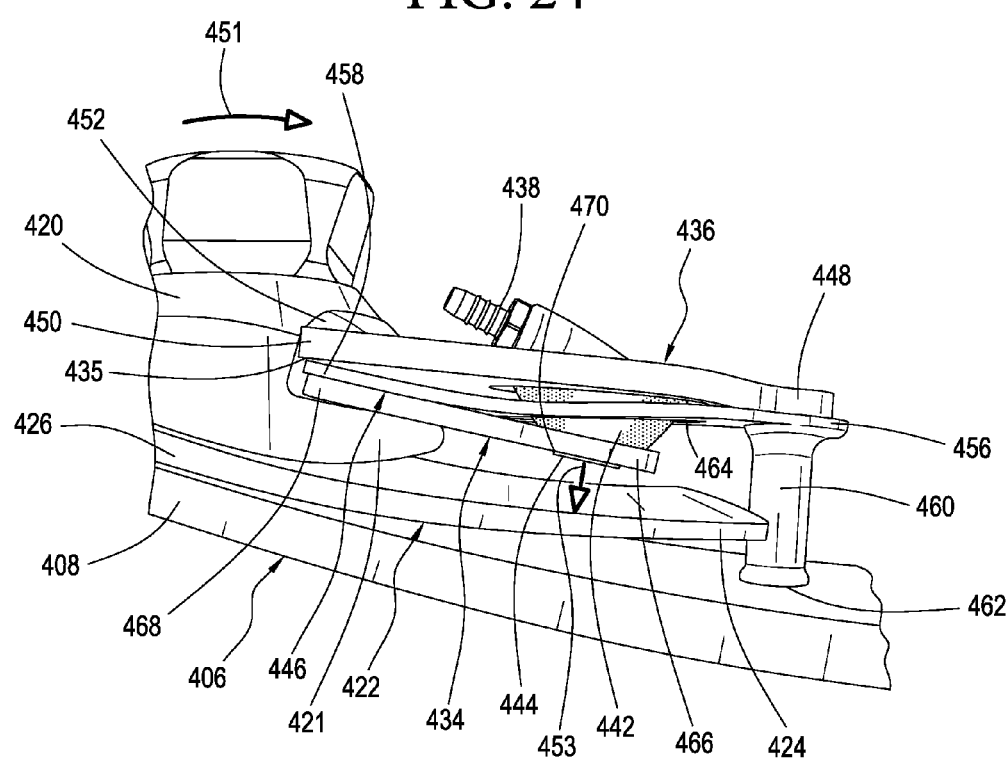
FIG. 25 shows a partial perspective side view of the prosthetic device in FIG. 23 in a second position.

An eighth embodiment of a prosthetic device 15 is shown in FIGS. 23-25. The prosthetic device 15 can include a pump mechanism 402 and a prosthetic foot 404. The prosthetic foot 404 has an upper foot member 422, a heel or lower foot member 414, and a middle foot member 406 disposed between the upper and lower foot members 422, 414.

The upper foot member 422 extends from a first end portion 426 terminating at a first end to a second end portion 424 terminating at a second end. The second end of the second end portion 424 is spaced a distance from the upper surface of the middle foot member 406 such that a variable gap is defined therebetween.

The middle foot member 406 is disposed below the upper foot member 422. The middle foot member 406 extends from a first end portion 408 terminating at a first end to a second end portion 410 terminating at a second end. The middle foot member 406 can define an intermediate portion 412 between the first end portion 408 and the second end portion 410. The intermediate portion 412 can have a flexible configuration. The intermediate portion 412 can define a curvature. The first end portion 408 of the middle foot member 406 is coupled to the first end portion 426 of the upper foot member 422.

The lower foot member 414 is disposed generally below the middle foot member 406. The lower foot member 414 can extend from a first end portion 416 terminating at a first end to second end portion 418 terminating at a second end.

The first end portion 416 of the lower foot member 414 can define a heel portion extending rearwardly to the first end and generally disposed below at least a portion of the middle foot member 406. The first end portion 416 can have a curvilinear profile along its length. The second end portion 418 can define a toe portion extending beyond the second end of the middle foot member 406. The middle foot member 406 is coupled to the lower foot member 414 via fasteners 428 proximate to the second end of the middle foot member 406.

An adaptor 420 can be coupled to the first end portion 426 of the upper foot member 422 and/or the first end portion 408 of the middle foot member 406. The adaptor 420 can be secured to an upper surface of the first end portion 426 of the upper foot member 422.

In use, the prosthetic foot can expand and compress via flexion of the middle foot member 406. The prosthetic foot 404 is in expansion when the first and second end portions of the middle foot member 406 are moved apart from a resting position of the foot 404, increasing the distance between the first and second end portions of the middle foot member 406. The prosthetic foot 404 is in compression when the first and second end portions of the middle foot member 406 are moved toward one another from the resting position of the foot 404, reducing the distance between the first and second end portions of the middle foot member 406.

The pump mechanism 402 can be coupled to the prosthetic foot at any suitable location but is shown coupled to the adaptor 420. The pump mechanism 402 is connected to the adaptor 420 and a movable member 434 is disposed below the pump mechanism 402. Similar to the other embodiments, movement of the movable member 434 can move or shift the pump mechanism 402 between an original configuration and an expanded configuration.

As best seen in FIGS. 24 and 25, the pump mechanism 402 includes a housing 436 containing two one-way valve assemblies 438, 440, a membrane 442, a connector 444, and a biasing mechanism or resilient member 446. The valve assembly 438 only allows fluid to enter the pump mechanism 402 which can be in fluid communication with the cavity of a socket. The valve assembly 440 (shown in FIG. 23) only allows fluid to be expelled out of the pump mechanism 402, preferably to atmosphere. The connector 444 can have any suitable configuration. For instance, the connector 444 can include an upper radial flange embedded in the membrane 442, a lower radial flange below the membrane 442, and a shaft portion extending between the upper and lower flanges.

Similar to the previously described pump mechanism embodiments, the pump mechanism 402 can rely upon deformation of the membrane 442 to move between an original configuration in which the volume of a fluid chamber defined between the top surface of the membrane 442 and the bottom of the housing 436 is zero or near-zero, an expanded configuration in which the volume of the fluid chamber is increased. The housing 436 is arranged to surround the outer radial edge portion of the membrane 442 and creates a seal with the membrane 442.

The bottom surface of the surface of the housing 436 defines a pair of openings which extend into housing 436 to form internal passageways to provide fluid communication between the fluid chamber and the two valve assemblies 438, 440.

The housing 436 is coupled to the adaptor 420 via at least one fastener 430 (shown in FIG. 23). The housing 436 can be pivotably coupled to the adaptor 420. The anterior section 421 of the adaptor 420 can define a recessed portion 452 arranged to facilitate attachment of the housing 436, the flexible member 446, and/or the movable member 434 to the adaptor 420. Optionally, a removable piece can be centrally secured to the adaptor 420 in the recessed portion 452. The housing 436 can have an elongate configuration defining an anterior section 448 and a posterior section 450. The posterior section 450 defines a pair of legs or arms positioned in the recessed portion 452 on opposing sides of the removable piece, helping to limit or prevent the housing 436 from sliding sideways off of the adaptor 420 and providing multiple contact points between the housing 436 and the adaptor 420. The posterior section 450 of the housing 436 can generally fit together with the anterior section 421 of adaptor 420, providing a sleek and low-profile design. It also generally does not substantially affect the functionality of the prosthetic foot 404. Furthermore, it should be appreciated that the pump mechanism 402 can be a separate add-on module to the prosthetic foot 404. In addition, the pump mechanism 402 can be adapted to fit a number of different prosthetic feet, providing versatility.

The resilient member 446 of the pump mechanism 402 is disposed below the housing 436. The resilient member 446 can be formed of any suitable material such as a metal material, composite, and/or resin material. The resilient member 446 is a plate having an elongate configuration defining an anterior section 456 attached to the anterior section 448 of the housing 436, and a posterior section 458 attached to the adaptor 420 and the posterior section of the housing 436 via the fastener 430. The resilient member 446 can extend beyond the anterior end of the upper foot member 422. The posterior end of the resilient member 446 can be positioned in a slot extending in a transverse direction through the adaptor 420.

The anterior section 456 of the resilient member 446 defines a bumper component 460 extending generally downward from the anterior section 456. The bumper component 460 can have any suitable configuration and has a lower end defining an engagement surface 462 arranged to engage with an upper surface of the middle foot member 406. The resilient member 446 defines an opening 464 that allows the connector 444 and membrane 442 to pass through the resilient member 446. As the prosthetic foot 404 moves between compression and expansion, the resilient member 446 is arranged to bend and flex between the bumper component 460 and the posterior section 458. The opening 464 can have an elliptical or elongate configuration. This allows for some movement of the resilient member 446 relative to the portion of the membrane 442 extending through the opening 464.

The movable member 434 can be a plate having a first portion or posterior end portion 468 and a second portion or anterior end portion 466. The posterior end portion 468 is secured below the resilient member 446 between the adaptor 420 and the resilient member 446. The anterior end portion 466 extends a distance above the upper foot member 422 from the posterior end portion 468. The anterior end portion 466 can define an opening 470 receiving the connector 444, which, in turn, couples the movable member 434 to the membrane 442. The movable member 434 can have a rigid and/or semi-rigid configuration. The movable member 434 can be fixed relative to the adaptor 420.

When the prosthetic foot 404 is in the resting position, the upper surface of the movable member 434 is substantially adjacent the lower surface of the resilient member 446 and the pump mechanism 402 is in its original configuration as seen in FIG. 24. Upon heel strike, the prosthetic foot moves into expansion and the pump mechanism 402 remains in its original configuration.

As the prosthetic foot 404 moves from heel strike through mid-stance and/or toe-off, the prosthetic foot 404 moves into compression as seen in FIG. 25. In compression, the first and second end portions 408, 410 of the middle foot member 406 move toward one another as generally indicated by arrow 451, causing the resilient member 446 to flex or bend between the bumper component 460 and the connection of the resilient member 446 to the adaptor 420.

The movement of the first and second end portions of the middle foot member 406 toward one another also causes the housing 436 to pivot about a pivot point 435 relative to the adaptor 420, separating the movable member 434 affixed to the adaptor 420 from the anterior section 448 of the housing 436 as generally indicated by arrow 453. This movement pulls the membrane 442 away from the housing 436, shifting the pump mechanism 402 to the expanded configuration. More particularly, the housing 436 and connector 444 coupled to the movable member 434 move apart, which, in turn, pulls the membrane 442 away from the housing 436 to deform the membrane 442 between the movable member 434 and the housing 436, increasing the volume of the fluid chamber. It will be appreciated that the housing 436 can move away from the movable member 434 and/or the movable member 434 can move away from the housing 436.

This increase in volume of the fluid chamber creates a vacuum in the pump mechanism 402, pulling fluid into the pump mechanism 402 through the one-way valve assembly 438. Compression of the prosthetic foot 404 thus can automatically create a vacuum in the pump mechanism 402.

At the end of the stance phase or when the weight of the user is removed from the prosthetic foot 404, the prosthetic foot 404 returns to its resting position and the energy stored in the resilient member 446 moves the housing 436 back toward its original position. This, in turn, moves the pump mechanism 402 back toward its original configuration and decreases the volume of the fluid chamber to a zero or near zero volume. During the return of the membrane 442 toward the housing 436, the pump mechanism 402 expels fluid in the fluid chamber out of the one-way valve 440.

It will be appreciated that the embodiments described herein are to be regarded as exemplary only, as any prosthetic device is possible. In other embodiments, the prosthetic device can include a movable member having a forked or split configuration that can create a vacuum at mid-stance, heel strike, and toe-off. For instance, a prosthetic device can include a prosthetic foot and a pump mechanism. The pump mechanism can include a housing, at least one one-way outlet valve assembly and at least one one-way inlet valve assembly, a first membrane, a first connector, a second membrane, and a second connector. The first connector can include an upper radial flange above the first membrane, a lower radial flange embedded in the first membrane, and a shaft portion extending between the upper and lower radial flanges. The second connector can include an upper radial flange embedded in the second membrane, a lower radial flange below the second membrane, and a shaft portion extending between the upper and lower flanges.

A portion of an upper surface of the housing can generally complement the lower surface of the adaptor on the prosthetic foot. Another portion of the upper surface of the housing can define a first cavity that is provided with an undercut circumferential groove between an open end of the first cavity and a closed bottom of the first cavity. An outer radial edge portion of the first membrane can be situated in the circumferential groove such that a seal is formed between the first membrane and the housing.

A bottom surface of the housing can define a second cavity that is provided with an undercut circumferential groove between an open end of the second cavity and a closed bottom of the second cavity. The bottom of each of the cavities can include openings which extend into the housing to form internal passageways providing fluid communication between fluid chambers defined below and the inlet and outlet valve assemblies.

The first membrane of the pump mechanism can be movable between an original configuration in which the volume of a first fluid chamber defined between the bottom surface of the first membrane and the bottom of the first cavity is zero or near-zero, and an expanded configuration in which the volume of the first fluid chamber is increased. The second membrane of the pump mechanism can also be movable between an original configuration in which the volume of a second fluid chamber defined between the upper surface of the second membrane and the bottom of the second cavity is zero or near-zero, and an expanded configuration in which the volume of the second fluid chamber is increased. Similar to the other embodiments, the pump mechanism relies upon deformation of the membranes to move between the original and expanded configurations.

The movable member can be an elongated plate including an anterior end portion and a posterior end portion. The anterior end portion can be attached to the prosthetic foot via a fastener. The fastener can be same fastener connecting the heel member to the prosthetic foot. The posterior end portion is arranged to connect to the membranes via the connectors and/or another fastener.

The movable member can have a forked or split configuration. For instance, the movable member can define first and second slots in a terminal edge of the posterior end portion that extend along a length of the movable member. The slots form a center blade and a pair of outer blades on the movable member. To attach the movable member to the first membrane, the center blade can be coupled to the first membrane. The center blade can be located between the upper surface of the first membrane and the first connector. To couple the movable member to the second membrane, the outer blades can be connected to the second membrane. The outer blades can be located between the lower surface of the second membrane and the second connector. It will be appreciated that in other embodiments, the outer blade can be coupled to the first membrane and the center blade can be coupled to the second membrane. The blades of the movable member can engage an anterior edge of the housing.

When the prosthetic foot is in the resting position, both the first membrane and the second membrane can be in the original configuration. Upon heel strike, the prosthetic foot moves into expansion, which, in turn, causes the outer blades to flex or pivot away from the housing about a pivot point. As the outer blades pivot away from the housing, the outer blades pull the second membrane away from the housing, moving the second membrane to the expanded configuration. More particularly, the outer blades pull the second membrane away from the housing to deform the second membrane between the outer blades of the movable member and the housing, increasing the volume of the second fluid chamber.

This increase in volume of the second fluid chamber creates a vacuum in the second fluid chamber, pulling fluid into the second fluid chamber through the inlet valve assembly. Expansion of the prosthetic foot thus automatically creates a vacuum in the pump mechanism.

As the prosthetic foot moves from heel strike back toward its resting position, the properties of the movable member can help return the outer blades to their un-flexed state, moving the second membrane back towards its original configuration and decreasing the volume of the second fluid chamber and decreasing the volume of the second fluid chamber to a zero or near-zero volume. During the return of the second membrane toward the housing, the pump mechanism can expel fluid from the second fluid chamber out of a valve assembly.

As the prosthetic foot moves from its resting position through mid-stance and/or toe-off, the prosthetic foot moves into compression. In compression, the center blade flexes or pivots away from the housing about the pivot point. As the center blade pivots away from the housing, the center blade pulls the first membrane away from the housing, moving the first membrane to the expanded configuration. More particularly, the center blade pulls the first membrane away from the housing to deform the first membrane between the center blade and the housing, increasing the volume of the first fluid chamber.

This increase in volume of the first fluid chamber creates a vacuum in the first fluid chamber, pulling fluid into the second fluid chamber through the inlet valve assembly.

In compression, the outer blades of the movable member also pivot toward the housing about the pivot point. As the outer blades pivot toward the housing, the outer blades force the second membrane toward the housing, moving the second membrane toward its original configuration and decreasing the volume of the second fluid chamber to a zero or near-zero volume. During the return of the second membrane toward the housing, the pump mechanism expels fluid in the second fluid chamber out of one of the outlet valve assemblies.

Compression of the prosthetic foot thus automatically creates a vacuum in the pump mechanism, pulling fluid into the pump mechanism from the socket, and simultaneously expels fluid from the pump mechanism to atmosphere, increasing the efficiency of the pump mechanism.

At the end of the stance phase or when the weight of the user is removed from the prosthetic foot, the prosthetic foot returns to its resting position and the properties of the movable member can help return the movable member to its un-flexed state, moving the first membrane back toward its original configuration and decreasing the volume of the first fluid chamber to a zero or near zero volume. During the return of the first membrane toward the housing, the pump mechanism expels fluid from the first fluid chamber out of the outlet valve assembly.

The pump mechanism advantageously can thus be activated during heel-strike, mid stance, and toe-off. More particularly, depending on whether the prosthetic foot is in compression or expansion, the movable member will pull one or the other membrane on the pump mechanism, creating a vacuum.

In other embodiments, the pump mechanism can be a piston-type pump that draws a vacuum at heel strike, mid-stance, and/or toe-off. For instance, a prosthetic device can include a prosthetic foot and a pump mechanism having a housing defining a cavity and a rod attached to a piston that reciprocates within the cavity. The piston can be arranged to separate the cavity into a first fluid chamber and a second fluid chamber.

The pump mechanism is shown including four one-way valve assemblies but may include any suitable number of valve assemblies. The valve assembly can only allow fluid to enter the first fluid chamber and can be connected to a tube. When the volume of the first fluid chamber increases, fluid can be drawn out from the socket via the valve assembly. The valve assembly is arranged to only allow fluid to be expelled out of the first fluid chamber. The valve assembly can be positioned within a channel defined within the rod.

The valve assembly is arranged to only allow fluid to enter the second fluid chamber and can be connected to a tube. When the volume of the second fluid chamber increases, fluid can be drawn out from the socket via the valve assembly. The valve assembly is arranged to only allow fluid to be expelled out of the second fluid chamber.

A movable member can be an arcuate plate including an anterior end portion and a posterior end portion. The anterior end portion can be attached to the prosthetic foot at or near the anterior end of the upper foot member via a fastener or other suitable means. The posterior end portion can be attached to the adaptor on the prosthetic foot. An upper surface of the housing generally complements and engages the curvature of the movable member. The movable member can be connected to the prosthetic foot such that the movable member is located between the prosthetic foot and the pump mechanism. The curvature of the movable member can generally complement the curvature of the anterior surface of the upper foot member. The rod is attached to the movable member between the anterior and posterior end portions.

Upon heel strike, the prosthetic foot moves to the expanded position, which, in turn, increases the radius of curvature of the movable member as the first and second end portions of the upper and lower foot members move apart. This increase of the radius of curvature or straightening out of the movable member pushes the rod and the piston away from the movable member, increasing the volume of the second fluid chamber. As the volume of the second fluid chamber increases, a vacuum is created that can pull fluid into the second fluid chamber through the valve assembly.

The movement of the rod and the piston away from the movable member also decreases the volume of the first fluid chamber, expelling fluid from the first fluid chamber out of the valve assembly.

As the prosthetic foot moves from heel strike through mid-stance and/or toe-off, the prosthetic foot moves into compression. In compression, the first and second end portions of the foot members move toward one another causing the radius of curvature of the movable member to decrease, which in turn, pulls the rod and the piston toward the movable member. This increases the volume of the first fluid chamber, creating a vacuum that can pull fluid into the first fluid chamber through the valve assembly. It also decreases the volume of the second fluid chamber, expelling fluid from the second fluid chamber out of the valve assembly. At the end of the stance phase, the prosthetic foot returns to its resting position and the properties of the movable member can help maintain the pump in an original configuration.

The pump mechanism can thus generate a vacuum in a socket at heel strike, mid-stance, and/or toe-off, creating a better attachment between the residual limb and the socket.

While the prosthetic foot is described in some embodiments including dual foot blades or foot members, in other embodiments, the prosthetic foot can include a single foot blade or foot member. Furthermore, while the movable member is described being attached to the membrane via a connector embedded in the membrane, in other embodiments, the movable member can be attached to the membrane via any suitable manner. While the valve assemblies are described being attached to the housing, in other embodiments, one or more of the valve assemblies can be in fluid communication with the pump mechanism via a tubular fluid conduit. It will be appreciated that the movable member can be made of any suitable material such as carbon fiber cloth, unidirectional composites, plastic, or metal.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic system comprising:
   a prosthetic foot including a foot member having a flexible configuration and defining a first end portion, a second end portion, and an intermediate portion defining a curvature and extending between the first and second end portions, and an adaptor attached to the first end portion of the foot member; and
   a pump mechanism positioned between the first and second end portions of the foot member, the pump mechanism including a housing secured to the adaptor and defining a cavity, and a membrane situated in the cavity, the pump mechanism movable between an original configuration in which the volume of a fluid chamber defined between the membrane and a bottom of the cavity is zero or near-zero, and an expanded configuration in which the volume of the fluid chamber is increased; and
   a movable member including a first portion coupled to the membrane and a second portion engaging the adaptor or a dorsal aspect of the foot member, wherein relative movement between the first and second end portions of the foot member moves the first portion of the movable member relative to the housing to shift the pump mechanism between the original configuration and the expanded configuration.

2. The prosthetic system of claim 1, wherein the movable member comprises a plate and the first portion comprises a posterior end portion and the second portion comprises an anterior end portion.

3. The prosthetic system of claim 1, wherein the movable member includes a clip mechanism arranged to selectively clip the movable member to the housing.

4. The prosthetic system of claim 3, wherein the housing defines a seat having a recessed configuration and arranged to accommodate a posterior end section of the clip mechanism.

5. The prosthetic system of claim 1, wherein the movable member biases the pump mechanism toward the original configuration.

6. The prosthetic system of claim 1, wherein the housing is removably attached to the adaptor.

7. The prosthetic system of claim 1, wherein the first portion of the movable member pivots relative to the housing to move the pump mechanism between the original configuration and the expanded configuration.

8. The prosthetic system of claim 7, wherein the first portion of the movable member is arranged to pivot around an anterior edge of the housing.

9. The prosthetic system of claim 1, wherein movement of the first and second end portions toward one another from a resting position moves the first portion of the movable member away from the housing and shifts the pump mechanism toward the expanded configuration.

10. The prosthetic system of claim 9, wherein movement of the first and second end portions of the foot member toward the resting position shifts the pump mechanism toward the original configuration.

11. The prosthetic system of claim 1, wherein the movable member comprises a plate and a terminal edge of the first portion defines a slot arranged to receive a connector coupling the movable member to the membrane.

12. The prosthetic system of claim 11, wherein the connector is arranged to slide within the slot as the first portion of the movable member moves relative to the housing.

13. The prosthetic system of claim 1, wherein the first portion of the movable member is attached to the membrane via a fastener.

14. The prosthetic system of claim 1, wherein the movable member is attached to the housing.

15. The prosthetic system of claim 1, wherein the movable member comprises a flexible enclosure having an elliptical configuration.

16. The prosthetic system of claim 1, further comprising:
a prosthetic socket in fluid communication with the pump mechanism and connected to the prosthetic foot.

17. The prosthetic system of claim 16, further comprising a tube connecting an interior of the prosthetic socket to a one-way valve assembly of the pump mechanism, the pump mechanism arranged to draw air from the interior of the prosthetic socket upon expansion of the pump mechanism.

18. A prosthetic system comprising:
a prosthetic foot including a foot member having a flexible configuration and defining a first end portion, a second end portion, and an intermediate portion defining a curvature and extending between the first and second end portions, and an adaptor attached to the first end portion of the foot member; and
a pump mechanism coupled to the foot member and positioned between the first and second end portions of the foot member, the pump mechanism including a housing secured to the adaptor and defining a cavity, and a membrane situated in the cavity, the pump mechanism movable between an original configuration in which the volume of a fluid chamber defined between the membrane and a bottom of the cavity is zero or near-zero, and an expanded configuration in which the volume of the fluid chamber is increased; and
a movable member including a first portion coupled to the membrane and a second portion engaging the adaptor or a dorsal aspect of the foot member; and
a prosthetic socket in fluid communication with the pump mechanism and connected to the prosthetic foot,
wherein flexion of the foot member moves the first portion of the movable member to shift the pump mechanism between the original configuration and the expanded configuration and draw fluid out of the prosthetic socket.

19. The prosthetic system of claim 18, wherein the movable member biases the pump mechanism toward the original configuration.

20. The prosthetic system of claim 18, wherein the movable member comprises a plate and the first portion comprises a posterior end portion and the second portion comprises an anterior end portion.

* * * * *